US006270961B1

(12) United States Patent
Drmanac

(10) Patent No.: US 6,270,961 B1
(45) Date of Patent: *Aug. 7, 2001

(54) METHODS AND APPARATUS FOR DNA SEQUENCING AND DNA IDENTIFICATION

(75) Inventor: Radoje Drmanac, Sunnyvale, CA (US)

(73) Assignee: Hyseq, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/353,554

(22) Filed: Dec. 9, 1994

Related U.S. Application Data

(63) Continuation-in-part of application No. 08/203,502, filed on Feb. 28, 1994, now Pat. No. 5,525,464, which is a continuation of application No. 08/048,152, filed on Apr. 15, 1993, now abandoned, which is a continuation of application No. 07/576,559, filed on Aug. 31, 1990, now abandoned, which is a continuation-in-part of application No. 07/175,088, filed on Mar. 30, 1988, now abandoned.

(30) Foreign Application Priority Data

Apr. 19, 1987 (YU) ..................................................... 570/87
Sep. 18, 1987 (YU) ..................................................... 570/87

(51) Int. Cl.[7] .............................. C12Q 1/68; C12Q 1/70; C12P 19/34; C07H 21/02
(52) U.S. Cl. ................................ 435/6; 435/5; 435/91.2; 436/518; 536/24.3; 536/24.31; 536/24.32; 536/24.33
(58) Field of Search ..................................... 435/5, 6, 912; 436/518; 536/24.3, 24.31, 24.32, 24.33

(56) References Cited

U.S. PATENT DOCUMENTS

| | | | |
|---|---|---|---|
| 4,591,567 | 5/1986 | Britten et al. | 435/293 |
| 4,775,631 | * 10/1988 | Saman | 435/6 |
| 4,883,750 | 11/1989 | Whiteley et al. | 435/6 |
| 5,143,854 | 9/1992 | Pirrung et al. | 436/518 |

(List continued on next page.)

FOREIGN PATENT DOCUMENTS

| | | |
|---|---|---|
| 152 886 A2 | 8/1985 | (EP) . |
| WO 89/10977 | 11/1989 | (WO) . |
| WO 90/04652 | 5/1990 | (WO) . |
| WO 94/27719 | 12/1994 | (WO) . |

OTHER PUBLICATIONS

Saiki et al, "Analysis of enzymatically amplified b–globin and HLA–DQalpha DNA with allele specific oligonucleotide probes", Nature 324:163–166, Nov. 1986.*

Ng et al, "Methods for analysis of multiple cystic fibrosis mutations", Human Genetics 87:613–617, 1991.*

Broude et al., "Enhanced DNA sequencing by hybridization", Proc. Natl. Acad. Sci. USA, 91:3072–3076 (Apr. 1994).

Dyer et al., "The Probability of Unique Solutions of Sequencing by Hybridization", J. Comp. Biol., 1(2):105–110 (Nov. 2, 1994).

Mirzabekov, DNA sequencing by hybridization—a megasequencing method and a diagnostic tool, Tibtech, 12:27–32 (Jan. 1994).

Bains, et al., "A Novel Method for Nucleic Acid Sequence Determination," J. Theor. Biol., 135:303–307 (1988).

Chissoe, et al., "Strategies for Rapid and Accurate DNA Sequencing," Methods: A Comparison to Methods in Enzymology, 3:55–65 (1991).

Drmanac, R., et al., "A Sequencing by Hybridization Towards an Automated Sequencing of One Million M13 Clones Arrayed on Membranes," Electrophoresis, 13, 566–573 (1992).

Drmanac, R., et al., "An Algorithm for the DNA Sequence Generation from a K–tuple word Contents of the Minimal Number of Random Fragments," J. Biomol. Struct. Dyn., 5:1085 (1991).

Drmanac, R., et al., "DNA Sequencing Determination by Hybridization: A Strategy for Efficient Large–Scale Sequencing," Science, 260:1649–1652 (1993).

Drmanac, R., et al., "Partial Sequencing by Oligohybridization: Concept and Applications in Genome Analysis," Proceedings of the First International Conference on Electrophoresis, Supercomputing, and the Human Genome, 60–75 (1991).

Drmanac, R., et al., "Processing of cDNA and Genomic Kilobase–Size Clones for massive Screening, Mapping, and Sequencing by Hybridization," Biotechniques, 17:328–335 (1994).

Drmanac, R., et al., "Prospects for a Miniaturized, Simplified, and Frugal Human Genome Project," Scientia Yugoslavica, 161(1–2):97–107 (1990).

(List continued on next page.)

Primary Examiner—Jeffrey Fredman
(74) Attorney, Agent, or Firm—Marshall, O'Toole, Gerstein, Murray & Borun

(57) ABSTRACT

Sequencing by Hybridization (SBH) methods and apparatus employing subdivided filters for discrete multiple probe analysis of multiple samples may be used for DNA identification and for DNA sequencing. Partitioned filters are prepared. Samples are affixed to sections of partitioned filters and each sector is probed with a single probe or a multiplexed probe for hybridization scoring. Hybridization data is analyzed for probe complementarity, partial sequencing by SBH or complete sequencing by SBH.

37 Claims, No Drawings

U.S. PATENT DOCUMENTS

| | | | |
|---|---|---|---|
| 5,202,231 | 4/1993 | Drmanac et al. ........................ | 435/6 |
| 5,242,794 | 9/1993 | Whiteley et al. ........................ | 435/6 |
| 5,405,783 | 4/1995 | Pirrung et al. ........................ | 436/518 |
| 5,424,186 | 6/1995 | Fodor et al. ............................. | 435/6 |
| 5,445,934 | 8/1995 | Fodor et al. ............................. | 435/6 |
| 5,645,990 * | 7/1997 | Love et al. .............................. | 435/6 |

OTHER PUBLICATIONS

Drmanac, R., et al., "Reliable Hybridization of Oligonucleotides as Short as 6 Nucleotides in Length," *DNA and Cell Biology (formerly DNA)*, 9: 527 (1990).

Drmanac, R., et al., "SBH and the Integration of Complementary Approaches in the Mapping, Sequencing, and Understanding of Complex Genomes," Proc. of 2nd Int'l. Conf. on Bioinformatics, Supercomputing, and Complex Genome Analysis, 121–134 (1993).

Drmanac, R., et al., "Sequencing of Hybridization," *Automated DNA Sequencing and Analysis Techniques*, 29–36 (1994).

Drmanac, R., et al., "Sequencing by Hybridization (SBH) with Oligonucleotide Probes as an Integral Approach for the Analysis of Complex Genomes," *Int'l. J. Genome Res.* 1:59–79 (1992).

Drmanac, R., et al., "Sequencing of Megabase plus DNA by Hybridization: Theory of the Method," *Genomics*, 4:114 (1989).

Drmanac, R., et al., "W (A or T) Sequences as a Source of Probes and Primers Suitable for Genomic Mapping and Fingerprinting," *Nucl. Acids Res.* 19:5839 (1991).

Fodor, et al., "Oligonucleotide Arrays and Sequence Analysis by Hybridization," Genome Science & Technology in Genome Sequening and Analysis Conference V, 33 (C. Venter, ed. Oct., 1994).

Hunkapiller, et al., "Large–Scale DNA Sequencing," *Current Opinion in Biotech.*, 2:92–101 (1991).

Khrapko, et al., "An Oligonucleotide Hybridization Approach to DNA Sequencing," *FEBS*, 256:118–122 (1989).

Kieleczawa, et al., "DNA Sequencing by Primer Walking with Stings of Contiguous Hexamers," *Science*, 258:1787–1791 (1992).

Labat, I., et al., "Simulations of Ordering and Sequence Reconstruction of Random DNA Clones Hybridized with a Small Number of Oligomeric Probes," Proc. of 2nd Int'l Conf. on Bioinformations, Supercomputing, and Complex Genome Analysis, 555–565 (1993).*

Lehrach, H., et al., "A Hybridization Fingerprinting in Genome Mapping and Sequencing," *Genome Analysis 1, Genetic and Physical Mapping*, 39–81 (1991).*

Livshits, et al., "DNA Sequencing by Hybridization with Oligonucleotide Matrix (SHOM). The Theory of DNA Washing Out After Hybridization–Oligonucleotide Melting Point Determination," *Mol. Biol. Abs.*, 93–07347 (1992).*

Nelson, et al., "Sequencing Two DNA Templates in Five Channels By Digital Compression—DNA Sequencing," *Mol. Biol. Abs.*, 93–04247 (1992).*

Nizetic, D., et al., "An Improved Bacterial Colony Lysis Procedure Enables Direct DNA Hybridization Using Short (10, 11 bases) Oligonucleotides to Cosmids," *Nucl. Acids Res.* 19:182 (1991).*

Pevzner, et al., "Improved Chips for Sequencing by Hybridization," *J. Biomolecular Structure & Dynamics*, 9:399–410 (1991).*

Strezoska, Z., "DNA sequencing by hybridization: 100 bases read by a non–gel–based method," *Proc. Nat'l Acad. Sci. USA*, 88:10089–10093 (1991).*

Venter, et al., "Genome Sequence Analysis: Scientific Objectives and Practical Strategies," *TIBTECH*, 10:8–11 (Jan. 1992).*

Khrapko, et al., "A Method for DNA Sequencing by hybridization with oligonucleotide matrix," *J. DNA Sequencing and Mapping*, 1:375–388 (1990).*

* cited by examiner

METHODS AND APPARATUS FOR DNA SEQUENCING AND DNA IDENTIFICATION

CROSS-REFERENCE TO RELATED APPLICATIONS

This application is a continuation-in-part of U.S. application Ser. No. 08/203,502, filed Feb. 28, 1994, now issued as U.S. Pat. No. 5,525,464, which is a continuation of U.S. application Ser. No. 08/048,152, filed Apr. 15, 1993, now abandoned, which is a continuation of U.S. application Ser. No. 07/576,559, filed Aug. 31, 1990, now abandoned, which is a continuation-in-part of U.S. application Ser. No. 07/175,088, filed Mar. 30, 1988, now abandoned. Applicants claim priority under 35 U.S.C. §119 of Yugoslavian Application No. P-570/87 filed Apr. 1, 1987, and Yuogoslavian Application No. 18617-P 570/87 filed Sep. 18, 1987, certified copies of which were submitted in the parent application Ser. No. 07/175,088.

FIELD OF THE INVENTION

This invention relates in general to methods and apparatus for nucleic acid analysis, and, in particular to, methods and apparatus for DNA sequencing.

BACKGROUND

The rate of determining the sequence of the four nucleotides in DNA samples is a major technical obstacle for further advancement of molecular biology, medicine, and biotechnology. Nucleic acid sequencing methods which involve separation of DNA molecules in a gel have been in use since 1978. The only other proven method for sequencing nucleic acids is sequencing by hybridization (SBH).

The array-based approach of SBH does not require single base resolution in separation, degradation, synthesis or imaging of a DNA molecule. In the most commonly discussed variation of this method, using mismatch discriminative hybridization of short oligonucleotides K bases in length, lists of constituent K-mer oligonucleotides may be determined for target DNA. The sequence may be assembled through uniquely overlapping scored oligonucleotides.

In SBH sequence assembly, K–1 oligonucleotides which occur repeatedly in analyzed DNA fragments due to chance or biological reasons may be subject to special consideration. If there is no additional information, relatively small fragments of DNA may be fully assembled in as much as every base pair (bp) is read several times. In assembly of relatively longer fragments, ambiguities may arise due to repeated occurrence of a K–1 nucleotide. This problem does not exist if mutated or similar sequences have to be determined. Knowledge of one sequence may be used as a template to correctly assemble a similar one.

There are several approaches for sequencing by hybridization. In SBH Format 1, DNA samples are arrayed and labelled probes are hybridized with the samples. Replica membranes with the same sets of sample DNAs may be used for parallel scoring of several probes and/or probes may be multiplexed. Arraying and hybridization of DNA samples on the nylon membranes are well developed. Each array may be reused many times. Format 1 is especially efficient for batch processing large numbers of samples.

In SBH Format 2, probes are arrayed and a labelled DNA sample fragment is hybridized to the arrayed probes. In this case, the complete sequence of one fragment may be determined from simultaneous hybridization reactions with the arrayed probes. For sequencing other DNA fragments, the same oligonucleotide array may be reused. The arrays may be produced by spotting or in situ variant of Format 2, DNA anchors are arrayed and ligation is used to determine oligosequences present synthesis. Specific hybridization has been demonstrated. In a variant of Format 2, DNA anchors are arrayed and ligation is used to determine oligosequences present at the end of target DNA.

In Format 3, two sets of probes are used. One set may be in the form of arrays and another, labelled set is stored in multiwell plates. In this case, target DNA need not be labelled. Target DNA and one labelled probe are added to the arrayed set of probes. If one attached probe and one labelled probe both hybridize contiguously on the target DNA, they are covalently ligated, producing a sequence twice as long to be scored. The process allows for sequencing long DNA fragments, e.g. a complete bacterial genome, without DNA subcloning in smaller pieces.

In the present invention, SBH is applied to the efficient identification and sequencing one or more DNA samples in a short period of time. The procedure has many applications in DNA diagnostics, forensics, and gene mapping. It also may be used to identify mutations responsible for genetic disorders and other traits, to assess biodiversity and to produce many other types of data dependent on DNA sequence.

SUMMARY OF THE INVENTION

As mentioned above, Format 1 SBH is appropriate for the simultaneous analysis of a large set of samples. Parallel scoring of thousands of samples on large arrays may be applied to one or a few samples are in thousands of independent hybridization reactions using small pieces of membranes. The identification of DNA may involve 1–20 probes and the identification of mutations may in some cases involve more than 1000 probes specifically selected or designed for each sample. For identification of the nature of the mutated DNA segments, specific probes may be synthesized or selected for each mutation detected in the first round of hybridizations.

According to the present invention, DNA samples may be prepared in small arrays which may be separated by appropriate spacers, and which may be simultaneously tested with probes selected from a set of oligonucleotides kept in multiwell plates. Small arrays may consist of one or more samples. DNA samples in each small array may consist of mutants or individual samples of a sequence. Consecutive small arrays which form larger arrays may represent either replication of the same array or samples of a different DNA fragment. A universal set of probes consists of sufficient probes to analyze any DNA fragment with prespecified precision, e.g. with respect to the redundancy of reading each bp. These sets may include more probes than are necessary for one specific fragment, but fewer than are necessary for testing thousands of DNA samples of different sequence.

DNA or allele identification and a diagnostic sequencing process may include the steps of:
1) Selection of a subset of probes from a dedicated, representative or universal set to be hybridized with each of a plurality small arrays;
2) Adding a first probe to each subarray on each of the arrays to be analyzed in parallel;
3) Performing hybridization and scoring of the hybridization results;
4) Stripping off previously used probes and repeating remaining probes that are to be scored;

5) Processing the obtained results to obtain a final analysis or to determine additional probes to be hybridized;
6) Performing additional hybridizations for certain subarrays; and
7) Processing complete sets of data and computing obtaining a final analysis.

The present invention solves problems in fast identification and sequencing of a small number of nucleic acid samples of one type (e.g. DNA, RNA) and in parallel analysis of many sample types by using a presynthesized set of probes of manageable size and samples attached to a support in the form of subarrays. Two approaches have been combined to produce an efficient and versatile process for the determination of DNA identity, for DNA diagnostics, and for identification of mutations. For the identification of known sequences a small set of shorter probes may be used in place of a longer unique probe. In this case, there may be more probes to be scored, but a universal set of probes may be synthesized to cover any type of sequence. For example, a full set of 6-mers or 7-mers are only 4,096 and 16,384 probes, respectively.

Full sequencing of a DNA fragment may involve two levels. One level is hybridization of a sufficient set of probes that cover every base at least once. For this purpose, a specific set of probes may be synthesized for a standard sample. This hybridization data reveals whether and where mutations (differences) occur in non-standard samples. To determine the identity of the changes, additional specific probes may be hybridized to the sample. In another embodiment, all probes from a universal set may be scored.

A universal set of probes allows scoring of a relatively small number of probes per sample in a two step process without unacceptable expenditure of time. The hybridization process involves successive probings, in a first step of computing an optimal subset of probes to be hybridized first and, then, on the basis of the obtained results, a second step of determining additional probes to be scored from among those in the existing universal set.

The use of an array of sample arrays avoids consecutive scoring of many oligonucleotides on a single sample or on a small set of samples. This approach allows the scoring of more probes in parallel by manipulation of only one physical object. By combining the use of the subarray formed with the universal set of probes and the four step hybridization process, a DNA sample 1000 bp in length may be sequenced in a relatively short period of time. If the sample is spotted at 50 subarrays in an array and the array is reprobed 10 times, 500 probes may be scored. This number of probes is highly sufficient. In screening for the occurrence of a mutation, approximately 335 probes may be used to cover each base three times. If a mutation is present, several covering probes will be affected. These negative probes may map the mutation with a two base precision. To solve a single base mutation mapped with this precision, an additional 15 probes may be employed. These probes cover any base combination for the two questionable positions (assuming that deletions and insertions are not involved). These probes may be scored in one cycle on 50 subarrays which contain the given sample. In the implementation of a multiple label color scheme (multiplexing), two to six probes labelled with different fluorescent dyes may be used as a pool, thereby reducing the number of hybridization cycles and shortening the sequencing process.

In more complicated cases, there may be two close mutations or insertions. They may be handled with more probes. For example, a three base insertion may be solved with 64 probes. The most complicated cases may be approached by several steps of hybridization, and the selecting of a new set of probes on the basis of results of previous hybridizations.

If subarrays consists of tens or hundreds of samples of one type, then several of them may be found to contain one or more changes (mutations, insertions, or deletions). For each segment where mutation occurs, a specific set of probes may be scored. The total number of probes to be scored for a type of sample may be several hundreds. The scoring of replica arrays in parallel allow scoring of hundreds of probes in a relatively small number of cycles. In addition, compatible probes may be pooled. Positive hybridizations may be assigned to the probes selected to check particular DNA segments because these segments usually differ in 75% of their constituent bases.

By using a larger set of longer probes, longer targets may be conveniently analyzed. These targets may represent pools of shorter fragments such as pools of exon clones.

The multiple step approach, which minimizes the number of necessary probes, may employ a specific hybridization scoring method to define the presence of heterozygotes (sequence variants) in a genomic segment to be sequenced from a diploid chromosomal set. There are two possibilities: i) the sequence from one chromosome represents a basic type and the sequence from the other represents a new variant; or, ii) both chromosomes contain new, but different variants. In the first case, the scanning step designed to map changes gives a maximal signal difference of two-fold at the heterozygotic position. In the second case, there is no masking; only a more complicated selection of the probes for the subsequent rounds of hybridizations may be required.

Scoring two-fold signal differences required in the first case may be achieved efficiently by comparing corresponding signals with controls containing only the basic sequence type and with the signals from other analyzed samples. This approach allows determination of a relative reduction in the hybridization signal for each particular probe in the given sample. This is significant because hybridization efficiency may vary more than two-fold for a particular probe hybridized with different DNA fragments having its full match target. In addition, heterozygotic sites may affect more than one probe depending on the number of oligonucleotide probes. Decrease of the signal for two to four consecutive probes produces a more significant indication of heterozygotic sites. The leads may be checked by small sets of selected probes among which one or few probes are suppose to give full match signal which is on average eight-fold stronger than the signals coming from mismatch-containing duplexes.

Partitioned membranes allow a very flexible organization of experiments to accommodate relatively larger numbers of samples representing a given sequence type, or many different types of samples represented with smaller number of samples. A range of 4–256 samples can be handled with particular efficiency. Subarrays within this range of numbers of dots may be designed to match the configuration and size of standard multiwell plates used for storing and labelling oligonucleotides. The size of the subarrays may be adjusted for different number of samples, or a few standard subarray sizes may be used. If all samples of one type do not fit in one subarray, additional subarrays or membranes may be used and processed with the same probes. In addition, by adjusting the number of replicas for each subarray, the time for completion of identification or sequencing process may be varied.

DETAILED DESCRIPTION

EXAMPLE 1

Preparation of a Universal Set of Probes

Two types of universal sets of probes may be prepared. The first is a complete set (or at least a noncomplementary subset) of relatively short probes. For example, all 4096 (or about 2000 non-complementary) 6-mers, or all 16,384 (or about 8,000 non-complementary) 7-mers. Full noncomplementary subsets of 8-mers and longer probes are less convenient in as much as they include 32,000 or more probes.

A second type of probe set is selected as a small subset of probes still sufficient for reading every bp in any sequence with at least with one probe. For example, 12 of 16 dimers are sufficient. A small subset for 7-mers, 8-mer and 9-mers for sequencing double stranded DNA may be about 3000, 10,000 and 30,000 probes, respectively.

Probes may be prepared using standard chemistry with one to three non-specified (mixed A,T,C and G) or universal (e.g. M base, inosine) bases at the ends. If radiolabelling is used, probes may have an OH group at the 5' end for kinasing by radiolabelled phosphorous groups. Alternatively, probes labelled with fluorescent dyes may be employed. Other types of probes like PNA (Protein Nucleic Acids)or probes containing modified bases which change duplex stability also may be used.

Probes may be stored in barcoded multiwell plates. For small numbers of probes, 96-well plates may be used; for 10,000 or more probes, storage in 384- or 864-well plates is preferred. Stacks of 5 to 50 plates are enough to store all probes. Approximately 5 pg of a probe may be sufficient for hybridization with one DNA sample. Thus, from a small synthesis of about 50 $\mu$g per probe, ten million samples may be analyzed. If each probe is used for every third sample, and if each sample is 1000 bp in length, then over 30 billion bases (10 human genomes) may be sequenced by a set of 5,000 probes.

EXAMPLE 2

Preparation of DNA Samples

DNA fragments may be prepared as clones in M13, plasmid or lambda vectors and/or prepared directly from genomic DNA or cDNA by PCR or other amplification methods. Samples may be prepared or dispensed in multi-well plates. About 100–1000 ng of DNA samples may be prepared in 2–500 $\mu$l of final volume.

EXAMPLE 3

Preparation of DNA Arrays

Arrays may be prepared by spotting DNA samples on a support such as a nylon membrane. Spotting may be performed by using arrays of metal pins (the positions of which correspond to an array of wells in a microtiter plate) to repeated by transfer of about 20 nl of a DNA solution to a nylon membrane. By offset printing, a density of dots higher than the density of the wells is achieved. One to 25 dots may be accommodated in 1 mm$^2$ depending on the type of label used. By avoiding spotting in some preselected number of rows and columns, separate subsets (subarrays) may be formed. Samples in one subarray may be the same genomic segment of DNA (or the same gene) from different individuals, or may be different, overlapped genomic clones. Each of the subarrays may represent replica spotting of the same samples. In one example, one gene segment may be amplified from 64 patients. For each patient, the amplified gene segment may be in one 96-well plate (all 96 wells containing the same sample). A plate for each of the 64 patients is prepared. By using a 96-pin device all samples may be spotted on one 8×12 cm membrane. Subarrays may contain 64 samples, one from each patient. Where the 96 subarrays are identical, the dot span may be 1 mm$^2$ and there may be a 1 mm space between subarrays.

Another approach is to use membranes or plates (available from NUNC, Naperville, Ill.) which may be partitioned by physical spacers e.g. a plastic grid molded over the membrane, the grid being similar to the sort of membrane applied to the bottom of multiwell plates, or hydrophobic strips. A fixed physical spacer is not preferred for imaging by exposure to flat phosphor-storage screens or x-ray films.

EXAMPLE 4

Selection and Labelling of Probes

When an array of subarrays is produced, the sets of probes to be hybridized in each of the hybridization cycles on each of the subarrays is defined. For the samples in Example 3, a set of 384 probes may be selected from the universal set, and 96 probings may be performed in each of 4 cycles. Probes selected to be hybridized in one cycle preferably have similar G+C contents.

Selected probes for each cycle are transferred to a 96-well plate and then are labelled by kinasing or by other labelling procedures if they are not labelled (e.g. with stable fluorescent dyes) before they are stored.

On the basis of the first round of hybridizations, a new set of probes may be defined for each of the subarrays for additional cycles. Some of the arrays may not be used in some of the cycles. For example, if only 8 of 64 patient samples exhibit a mutation and 8 probes are scored first for each mutation, then all 64 probes may be scored in one cycle and 32 subarrays are not used. These subarrays may then be treated with hybridization buffer to prevent drying of the filters.

Probes may be retrieved from the storing plates by any convenient approach, such as a single channel pipetting device or a robotic station such as a Beckman Biomek 1000 (Beckman Instruments, Fullerton, Calif.) or a Mega Two robot (Megamation, Lawrenceville, N.J.). A robotic station may be integrated with data analysis programs and probe managing programs. Outputs of these programs may be inputs for one or more robotic stations.

Probes may be retrieved one by one and added to subarrays covered by hybridization buffer. It is preferred that retrieved probes be placed in a new plate and labelled or mixed with hybridization buffer. The preferred method of retrieval is by accessing stored plates one by one and pipetting (or transferring by metal pins) a sufficient amount of each selected probe from each plate to specific wells in an intermediary plate. An array of individually addressable pipettes or pins may be used to speed up the retrieval process.

EXAMPLE 5

Hybridization and Scoring Process

Labelled probes may be mixed with hybridization buffer and pipetted preferentially by multichannel pipettes to the subarrays. To prevent mixing of the probes between subarrays (if there are no hydrophilic strips or physical barriers imprinted in the membrane), a corresponding plastic, metal or ceramic grid may be firmly pressed to the membrane. Also, the volume of the buffer may be reduced to about 1 $\mu$l or less per mm$^2$. The concentration of the probes and hybridization conditions used may be as described previously except that the washing buffer may be quickly poured over the array of subarrays to allow fast dilution of probes and thus prevent significant cross-hybridization. For the same reason, a minimal concentration of the probes may be used and hybridization time extended to the maximal practical level. For DNA detection and sequencing, knowledge of a "normal" sequence allows the use of the continuous stacking interaction phenomenon to increase the signal. In addition to the labelled probe, additional unlabelled probes which hybridize back to back with a labelled one may be added in the hybridization reaction. The amount of the hybrid may be increased several times. The probes may be connected by ligation. This approach may be important for resolving DNA regions forming "compressions".

In the case of radiolabelled probes, images of the filters may be obtained preferentially by phosphorstorage technology. Fluorescent labels may be scored by CCD cameras, confocal microscopy or otherwise. Raw signals are normalized based on the amount of target in each dot to properly scale and integrate data from different hybridization experiments. Differences in the amount of target DNA per dot may be corrected for by dividing signals of each probe by an average signal for all probes scored on one dot. Also, the normalized signals may be scaled, usually from 1–100, to compare data from different experiments. Also, in each subarray, several control DNAs may be used to determine an average background signal in those samples which do not contain a full match target. Furthermore, for samples obtained from diploid (polyploid) scores, homozygotic controls may be used to allow recognition of heterozygotes in the samples.

EXAMPLE 6

Diagnostics—Scoring Known Mutations or Full Gene Resequencing

A simple case is to discover whether some known mutations occur in a DNA segment. Less than 12 probes may suffice for this purpose, for example, 5 probes positive for one allele, 5 positive for the other, and 2 negative for both. Because of the small number of probes to be scored per sample, large numbers of samples may be analyzed in parallel. For example, with 12 probes in 3 hybridization cycles, 96 different genomic loci or gene segments from 64 patient may be analyzed on one 6×9 in membrane containing 12×24 subarrays each with 64 dots representing the same DNA segment from 64 patients. In this example, samples may be prepared in sixty-four 96-well plates. Each plate may represent one patient, and each well may represent one of the DNA segments to be analyzed. The samples from 64 plates may be spotted in four replicas as four quarters of the same membrane.

A set of 12 probes may be selected by single channel pipetting or a single pin transferring device (or by an array of individually controlled pipets or pins) for each of the 96 segments and rearranged in twelve 96-well plates. Probes may be labelled if they are not prelabelled before storing, and then probes from four plates may be mixed with hybridization buffer and added to the subarrays preferentially by a 96-channel pipeting device. After one hybridization cycle it is possible to strip off previously used probes by incubating the membrane at 37° to 55° C. in the preferably undiluted hybridization or washing buffer.

The likelihood that probes positive for one allele are positive and probes positive for the other allele are negative may be used to determine which of the two allels is present. In this redundant scoring scheme, some level (about 10%) of errors in hybridization of each probe may be tolerated.

An incomplete set of probes may be used for scoring most of the alleles, especially if the smaller redundancy is sufficient, e.g. one or two probes which prove the presence or absence in a sample of one of the two alleles. For example, with a set of four thousand 8-mers there is a 91% chance of finding at least one positive probe for one of the two alleles for a randomly selected locus. The incomplete set of probes may be optimized to reflect G+C content and other biases in the analyzed samples.

For full gene sequencing, genes may be amplified in an appropriate number of segments. For each segment, a set of probes (about one probe per 2–4 bases) may be selected and hybridized. These probes may identify whether there is a mutation anywhere in the analyzed segments. Segments (i.e., subarrays which contain these segments) where one or more mutated sites are detected may be hybridized with additional probes to find the exact sequence at the mutated sites. If a DNA sample is tested by every second 6-mer, and a mutation is localized at the position that is surrounded by positively hybridized probes TGCAAA and TATTCC and covered by three negative probes: CAAAAC, AAACTA and ACTATT, the mutated nucleotides must be A and/or C occurring in the normal sequence at that position. They may be changed by a single base mutation, or by a one or two nucleotide deletion and/or insertion between bases AA, AC or CT.

One approach is to select a probe that extends the positively hybridized probe TGCAAA for one nucleotide to the right, and which extends the probe TATTCC one nucleotide to the left. With these 8 probes (GCAAAA, GCAAAT, GCAAAC, GCAAAG and ATATTC, TTATTC, CTATTC, GTATTC) two questionable nucleotides are determined.

The most likely hypothesis about the mutation may be determined. For example, A is found to be mutated to G. There are two solutions satisfied by these results. Either replacement of A with G is the only change or there is in addition to that change an insertion of some number of bases between newly determined G and the following C. If the result with bridging probes is negative these options may then be checked first by at least one bridging probe comprising the mutated position (AAGCTA) and with an additional 8 probes: CAAAGA, CAAAGT, CAAAGC, CAAAGG and ACTATT, TCTATT, CCTATT, GCTATT, I There are many other ways to select mutation-solving probes.

In the case of diploid, particular comparisons of scores for the test samples and homozygotic control may be performed to identify heterozygotes (see above). A few consecutive probes are expected to have roughly twice smaller signals if the segment covered by these probes is mutated on one of the two chromosomes.

EXAMPLE 7

Identification of Genes (Mutations) Responsible for Genetic Disorders and Other Traits The sequencing process disclosed herein has a very low cost per bp. Also, using larger universal sets of longer probes (8-mers or 9-mers), DNA fragments as long as 5–20 kb may be sequenced without subcloning. Furthermore, the speed of resequencing may be about 10 million bp/day/hybridization instrument. This performance allows for resequencing a large fraction of human genes or the human genome repeatedly from scientifically or medically interesting individuals. To resequence 50% of the human genes, about 100 million bp is checked. That may be done in a relatively short period of time at an affordable cost.

This enormous resequencing capability may be used in several ways to identify mutations and/or genes that encode for disorders or any other traits. Basically, mRNAs (which may be converted into cDNAs) from particular tissues or genomic DNA of patients with particular disorders may be used as starting materials. From both sources of DNA, separate genes or genomic fragments of appropriate length may be prepared either by cloning procedures or by in vitro amplification procedures (for example by PCR). If cloning is used, the minimal set of clones to be analyzed may be selected from the libraries before sequencing. That may be done efficiently by hybridization of a small number of probes, especially if a small number of clones longer than 5 kb is to be sorted. Cloning may increase the amount of hybridization data about two times, but does not require tens of thousands of PCR primers.

In one variant of the procedure, gene or genomic fragments may be prepared by restriction cutting with enzymes like Hga I which cuts DNA in following way: GACGC(N5')/ CTGCG(N10'). Protruding ends of five bases are different for different fragments. One enzyme produces appropriate fragments for a certain number of genes. By cutting cDNA or genomic DNA with several enzymes in separate reactions, every gene of interest may be excised appropriately. In one approach, the cut DNA is fractionated by size. DNA fragments prepared in this way (and optionally treated with Exonuclease III which individually removes nucleotides from the 3' end and increases length and specificity of the ends) may be dispensed in the tubes or in multiwell plates. From a relatively small set of DNA adapters with a common portion and a variable protruding end of appropriate length, a pair of adapters may be selected for every gene fragment that needs to be amplified. These adapters are ligated and then PCR is performed by universal primers. From 1000 adapters, a million pairs may be generated, thus a million different fragments may be specifically amplified in the identical conditions with a universal pair of primers complementary to the common end of the adapters.

If a DNA difference is found to be repeated in several patients, and that sequence change is nonsense or can change function of the corresponding protein, then the mutated gene may be responsible for the disorder. By analyzing a significant number of individuals with particular traits, functional allelic variations of particular genes could be associated by specific traits.

This approach may be used to eliminate the need for very expensive genetic mapping on extensive pedigrees and has special value when there is no such genetic data or material.

EXAMPLE 8

Scoring Single Nucleotide Polymorphisms in Genetic Mapping

Techniques disclosed in this application are appropriate for an efficient identification of genomic fragments with single nucleotide polymorphisms (SNUPs). In 10 individuals by applying the described sequencing process on a large number of genomic fragments of known sequence that may be amplified by cloning or by in vitro amplification, a sufficient number of DNA segments with SNUPs may be identified. The polymorphic fragments are further used as SNUP markers. These markers are either mapped previously (for example they represent mapped STSs) or they may be mapped through the screening procedure described below.

SNUPs may be scored in every individual from relevant families or populations by amplifying markers and arraying them in the form of the array of subarrays. Subarrays contain the same marker amplified from the analyzed individuals. For each marker, as in the diagnostics of known mutations, a set of 6 or less probes positive for one allele and 6 or less probes positive for the other allele may be selected and scored. From the significant association of one or a group of the markers with the disorder, chromosomal position of the responsible gene(s) may be determined. Because of the high throughput and low cost, thousands of markers may be scored for thousands of individuals. This amount of data allows localization of a gene at a resolution level of less than one million bp as well as localization of genes involved in polygenic diseases. Localized genes may be identified by sequencing particular regions from relevant normal and affected individuals to score a mutation(s).

PCR is preferred for amplification of markers from genomic DNA. Each of the markers require a specific pair of primers. The existing markers may be convertible or new markers may be defined which may be prepared by cutting genomic DNA by Hga I type restriction enzymes, and by ligation with a pair of adapters as described in Example 7.

SNUP markers can be amplified or spotted as pools to reduce the number of independent amplification reactions. In this case, more probes are scored per one sample. When 4 markers are pooled and spotted on 12 replica membranes, then 48 probes (12 per marker) may be scored in 4 cycles.

EXAMPLE 9

Detection and Verification of Identity of DNA Fragments

DNA fragments generated by restriction cutting, cloning or in vitro amplification (e.g. PCR) frequently may be identified in a experiment. Identification may be performed by verifying the presence of a DNA band of specific size on gel electrophoresis. Alternatively, a specific oligonucleotide may be prepared and used to verify a DNA sample in question by hybridization. The procedure developed here allows for more efficient identification of a large number of samples without preparing a specific oligonucleotide for each fragment. A set of positive and negative probes may be selected from the universal set for each fragment on the basis of the known sequences. Probes that are selected to be positive usually are able to form one or a few overlapping groups and negative probes are spread over the whole insert.

This technology may be used for identification of STSs in the process of their mapping on the YAC clones. Each of the STSs may be tested on about 100 YAC clones or pools of YAC clones. DNAs from these 100 reactions possibly are spotted in one subarray. Different STSs may represent consecutive subarrays. In several hybridization cycles, a signature may be generated for each of the DNA samples, which signature proves or disproves existence of the particular STS in the given YAC clone with necessary confidence.

To reduce the number of independent PCR reactions or the number of independent samples for spotting, several STSs may be amplified simultaneously in a reaction or PCR samples may be mixed, respectively. In this case more probes have to be scored per one dot. The pooling of STSs is independent of pooling YACs and may be used on single YACs or pools of YACs. This scheme is especially attractive when several probes labelled with different colors are hybridized together.

In addition to confirmation of the existence of a DNA fragment in a sample, the amount of DNA may be estimated using intensities of the hybridization of several separate probes or one or more pools of probes. By comparing obtained intensities with intensities for control samples having a known amount of DNA, the quantity of DNA in all spotted samples is determined simultaneously. Because only a few probes are necessary for identification of a DNA fragment, and there are N possible probes that may be used for DNA N bases long, this application does not require a large set of probes to be sufficient for identification of any DNA segment. From one thousand 8-mers, on average about 30 full matching probes may be selected for a 1000 bp fragment.

EXAMPLE 10

Identification of Infectious Disease Organisms and Their Variants

DNA-based tests for the detection of viral, bacterial, fungal and other parasitic organisms in patients are usually more reliable and less expensive than alternatives. The major advantage of DNA tests is to be able to identify specific strains and mutants, and eventually be able to apply more effective treatment. Two applications are described below.

The presence of 12 known antibiotic resistance genes in bacterial infections may be tested by amplifying these genes. The amplified products from 128 patients may be spotted in two subarrays and 24 subarrays for 12 genes may then be repeated four times on a 8×12 cm membrane. For each gene, 12 probes may be selected for positive and negative scoring. Hybridizations may be performed in 3 cycles. For these tests, as for the tests in Example 9, a much smaller set of probes is most likely to be universal. For example, from a set of one thousand 8-mers, on average 30 probes are positive in 1000 bp fragments, and 10 positive probes are usually sufficient for a highly reliable identification. As described in Example 9, several genes may be amplified and/or spotted together and the amount of the given DNA may be determined. The amount of amplified gene may be used as an indicator of the level of infection.

Another example involves possible sequencing of one gene or the whole genome of an HIV virus. Because of rapid diversification, the virus poses many difficulties for selection of an optimal therapy. DNA fragments may be amplified from isolated viruses from up to 64 patients and resequenced by the described procedure. On the basis of the obtained sequence the optimal therapy may be selected. If there is a mixture of two virus types of which one has the basic sequence (similar to the case of heterozygotes), the mutant may be identified by quantitative comparisons of its hybridization scores with scores of other samples, especially control samples containing the basic virus type only. Scores twice as small may be obtained for three to four probes that cover the site mutated in one of the two virus types present in the sample (see above).

EXAMPLE 11

Forensic and Parental Identification Applications

Sequence polymorphisms make an individual genomic DNA unique. This permits analysis of blood or other body fluids or tissues from a crime scene and comparison with samples from criminal suspects. A sufficient number of polymorphic sites are scored to produce a unique signature of a sample. SBH may easily score single nucleotide polymorphisms to produce such signatures.

A set of DNA fragments (10–1000) may be amplified from samples and suspects. DNAs from samples and suspects representing one fragment are spotted in one or several subarrays and each subarray may be replicated 4 times. In three cycles, 12 probes may determine the presence of allele A or B in each of the samples, including suspects, for each DNA locus. Matching the patterns of samples and suspects may lead to discovery of the suspect responsible for the crime.

The same procedure may be applicable to prove or disprove the identity of parents of a child. DNA may be prepared and polymorphic loci amplified from the child and adults; patterns of A or B alleles may be determined by hybridization for each. Comparisons of the obtained patterns, along with positive and negative controls, aide in the determination of familial relationships. In this case, only a significant portion of the alleles need match with one parent for identification. Large numbers of scored loci allow for the avoidance of statistical errors in the procedure or of masking effects of de novo mutations.

EXAMPLE 12

Assessing Genetic Diversity of Populations or Species and Biological Diversity of Ecological Niches Measuring the frequency of allelic variations on a significant number of loci (for example, several genes or entire mitochondrial DNA) permits development of different types of conclusions, such as conclusions regarding the impact of the environment on the genotypes, history and evolution of a population or its susceptibility to diseases or extinction, and others. These assessments may be performed by testing specific known alleles or by full resequencing of some loci to be able to define de novo mutations which may reveal fine variations or presence of mutagens in the environment.

Additionally, biodiversity in the microbial world may be surveyed by resequencing evolutionarily conserved DNA sequences, such as the genes for ribosomal RNAs or genes for highly conservative proteins. DNA may be prepared from the environment and particular genes amplified using primers corresponding to conservative sequences. DNA fragments may be cloned preferentially in a plasmid vector (or diluted to the level of one molecule per well in multiwell plates and than amplified in vitro). Clones prepared this way may be resequenced as described above. Two types of information are obtained. First of all, a catalogue of different species may be defined as well as the density of the individuals for each species. Another segment of information may be used to measure the influence of ecological factors or pollution on the ecosystem. It may reveal whether some species are eradicated or whether the abundance ratios among species is altered due to the pollution. The method also is applicable for sequencing DNAs from fossils.

EXAMPLE 13

DNA Sequencing

An array of subarrays allows for efficient sequencing of a small set of samples arrayed in the form of replicated subarrays; For example, 64 samples may be arrayed on a 8×8 mm subarray and 16×24 subarrays may be replicated on a 15×23 cm membrane with 1 mm wide spacers between the subarrays. Several replica membranes may be made. For example, probes from a universal set of three thousand seventy-two 7-mers may be divided in thirty-two 96-well plates and labelled by kinasing. Four membranes may be processed in parallel during one hybridization cycle. On each membrane, 384 probes may be scored. All probes may be scored in two hybridization cycles. Hybridization intensities may be scored and the sequence assembled as described below.

If a single sample subarray or subarrays contains several unknowns, especially when similar samples are used, a smaller number of probes may be sufficient if they are intelligently selected on the basis of results of previously scored probes. For example, if probe AAAAAAA is not positive, there is a small chance that any of 8 overlapping probes are positive. If AAAAAAA is positive, then two probes are usually positive. The sequencing process in this case consists of first hybridizing a subset of minimally overlapped probes to define positive anchors and then to successively select probes which confirms one of the most likely hypotheses about the order of anchors and size and type of gaps between them. In this second phase, pools of 2–10 probes may be used where each probe is selected to be positive in only one DNA sample which is different from the samples expected to be positive with other probes from the pool.

The subarray approach allows efficient implementation of probe competition (overlapped probes) or probe cooperation (continuous stacking of probes) in solving branching problems. After hybridization of a universal set of probes the sequence assembly program determines candidate sequence subfragments (SFs). For the further assembly of SFs, additional information has to be provided (from overlapped sequences of DNA fragments, similar sequences, single pass gel sequences, or from other hybridization or restriction mapping data). Competitive hybridization and continuous stacking interactions have been proposed for SF assembly. These approaches are of limited practical value for sequencing of large numbers of samples by SBH wherein a labelled probe is applied to a sample affixed to an array if a uniform array is used. Fortunately, analysis of small numbers of samples using replica subarrays allows efficient implementation of both approaches. On each of the replica subarrays, one branching point may be tested for one or more DNA samples using pools of probes similarly as in solving mutated sequences in different samples spotted in the same subarray (see above).

If in each of 64 samples described in this example, there are about 100 branching points, and if 8 samples are analyzed in parallel in each subarray, then at least 800 subarray probings solve all branches. This means that for the 3072 basic probings an additional 800 probings (25%) are employed. More preferably, two probings are used for one branching point. If the subarrays are smaller, less additional probings are used. For example, if subarrays consist of 16 samples, 200 additional probings may be scored (6%). By using 7-mer probes ($N_{1-2}B_7N_{1-2}$) and competitive or collaborative branching solving approaches or both, fragments of about 1000 bp fragments may be assembled by about 4000 probings. Furthermore, using 8-mer probes ($NB_8N$) 4 kb or longer fragments may be assembled with 12,000 probings. Gapped probes, for example, $NB_4NB_3N$ or $NB_4NB_4N$ may be used to reduce the number of branching points.

EXAMPLE 14

DNA Analysis by Transient Attachment to Subarrays of Probes and Ligation of Labelled Probes.

Oligonucleotide probes having an informative length of four to 40 bases are synthesized by standard chemistry and stored in tubes or in multiwell plates. Specific sets of probes comprising one to 10,000 probes are arrayed by deposition or in situ synthesis on separate supports or distinct sections of a larger support. In the last case, sections or subarrays may be separated by physical or hydrophobic barriers. The probe arrays may be prepared by in situ synthesis. A sample DNA of appropriate size is hybridized with one or more specific arrays. Many samples may be interrogated as pools at the same subarrays or independently with different subarrays within one support. Simultaneously with the sample or subsequently, a single labelled probe or a pool of labelled probes is added on each of the subarrays. If attached and labelled probes hybridize back to back on the complementary target in the sample DNA they are ligated. Occurrence of ligation will be measured by detecting a label from the probe.

This procedure is a variant of the described DNA analysis process in which DNA samples are not permanently attached to the support. Transient attachment is provided by probes fixed to the support. In this case there is no need for a target DNA arraying process. In addition, ligation allows detection of longer oligonucleotide sequences by combining short labelled probes with short fixed probes.

The process has several unique features. Basically, the transient attachment of the target allows its reuse. After ligation occur the target may be released and the label will stay covalently attached to the support. This feature allows cycling the target and production of detectable signal with a small quantity of the target. Under optimal conditions, targets do not need to be amplified, e.g. natural sources of the DNA samples may be directly used for diagnostics and sequencing purposes. Targets may be released by cycling the temperature between efficient hybridization and efficient melting of duplexes. More preferablly, there is no cycling. The temperature and concentrations of components may be defined to have an equilibrium between free targets and targets entered in hybrids at about 50:50% level. In this case there is a continuous production of ligated products. For different purposes different equilibrium ratios are optimal.

An electric field may be used to enhance target use. At the beginning, a horizontal field pulsing within each subarray may be employed to provide for faster target sorting. In this phase, the equilibrium is moved toward hybrid formation, and unlabelled probes may be used. After a target sorting phase, an appropriate washing (which may be helped by a vertical electric field for restricting movement of the samples) may be performed. Several cycles of discriminative hybrid melting, target harvesting by hybridization and ligation and removing of unused targets may be introduced to increase specificity. In the next step, labelled probes are added and vertical electrical pulses may be applied. By increasing temperature, an optimal free and hybridized target ratio may be achieved. The vertical electric field prevents diffusion of the sorted targets.

The subarrays of fixed probes and sets of labelled probes (specially designed or selected from a universal probe set) may be arranged in various ways to allow an efficient and flexible sequencing and diagnostics process. For example, if a short fragment (about 100–500 bp) of a bacterial genome is to be partially or completely sequenced, small arrays of probes (5–30 bases in length) designed on the bases of known sequence may be used. If interrogated with a different pool of 10 labelled probes per subarray, an array of 10 subarrays each having 10 probes, allows checking of 200 bases, assuming that only two bases connected by ligation are scored. Under the conditions where mismatches are discriminated throughout the hybrid, probes may be displaced by more than one base to cover the longer target with the same number of probes. By using long probes, the target may be interrogated directly without amplification or isolation from the rest of DNA in the sample. Also, several targets may be analyzed (screened for) in one sample simultaneously. If the obtained results indicate occurrence of a mutation (or a pathogen), additional pools of probes may be used to detect type of the mutation or subtype of pathogen. This is a desirable feature of the process which may be very cost effective in preventive diagnosis where only a small fraction of patients is expected to have an infection or mutation.

In the processes described in the examples, various detection methods may be used, for example, radiolabels, fluorescent labels, enzymes or antibodies (chemiluminescence), large molecules or particles detectable by light scattering or interferometric procedures.

EXAMPLE 15

Oligonucleotide Probes and Targets Suitable for SBH

In order to obtain experimental sequence data defined as a matrix of (number of fragments-clones)×(number of probes), the number of probes may be reduced depending on the number of fragments used and vice versa. The optimal ratio of the two numbers is defined by the technological requirements of a particular sequencing by hybridization process.

There are two parameters which influence the choice of probe length. The first is the success in obtaining hybridization results that show the required degree of discrimination. The second is the technological feasibility of synthesis of the required number of probes.

The requirement of obtaining sufficient hybridization discrimination with practical and useful amounts of target nucleic acid limits the probe length. It is difficult to obtain a sufficient amount of hybrid with short probes, and to discriminate end mismatches with long probes. Traditionally the use of probes shorter than 11-mers in the literature, is limited to very stable probes [Estivill et al., Nucl. Acids Res.15: 1415 (1987)] On the other hand, probes longer than 15 bases discriminate end mismatches with difficulty (Wood et al., Proc. Natl. Acad. Sci. USA 82: 1585 (1985)].

One solution for the problems of unstable probes and end mismatch discrimination is the use of a group of longer probes representing a single shorter probe in an informational sense. For example, groups of sixteen 10-mers may be used instead of single 8-mers. Every member of the group has a common core 8-mer and one of three possible variations on outer positions with two variations at each end. The probe may be represented as 5'(A, T, C, G) (A, T, C, G) $B_8$ (A, T, C, G) 3'. With this type of probe one does not need to discriminate the non-informative end bases (two on 5' end, and one on 3' end) since only the internal 8-mer is read. This solution employs a higher mass amounts of probes and label in hybridization reactions.

These disadvantages are eliminated by the use of a few sets of discriminative hybridization conditions for oligomer probes as short as 6-mers.

The number of hybridization reactions is dependent on the number of discrete labelled probes. Therefore in the cases of sequencing shorter nucleic acids using a smaller number of fragments-clones than the number of oligonucleotides, it is better to use oligomers as the target and nucleic acid fragment as probes.

Target nucleic acids which have undefined sequences may be produced as a mixture of representative libraries in a phage or plasmid vector having inserts of genomic fragments of different sizes or in samples prepared by PCR. Inevitable gaps and uncertainties in alignment of sequenced fragments arise from nonrandom or repetitive sequence organization of complex genomes and difficulties in cloning poisonous sequences in Escherichia coli. These problems are inherent in sequencing large complex molecules using any method. Such problems may be minimized by the choice of libraries and number of subclones used for hybridization. Alternatively, such difficulties may be overcome through the use of amplified target sequences, e.g. by PCR amplification, ligation reactions, ligation-amplified reactions, etc.

Nucleic acids and methods for isolating, cloning and sequencing nucleic acids are well known to those of skill in the art. See e.g., Ausubel et al., *Current Protocols in Molecular Biology*, Vol. 1–2, John Wiley & Sons (1989); and Sambrook et al., Molecular Cloning A Laboratory Manual, 2nd Ed., Vols. 1–3, Cold Springs Harbor Press (1989), both of which are incorporated by reference herein.

SBH is a well developed technology that may be practiced by a number of methods known to those skilled in the art. Specifically, techniques related to sequencing by hybridization of the following documents is incorporated by reference herein: Drmanac et al., U.S. Pat. No. 5,202,231 (hereby incorporated by reference herein)—Issued Apr. 13, 1993; Drmanac et al., *Genomics*, 4, 114–128 (1989); Drmanac et al., *Proceedings of the First Int'l. Conf. Electrophoresis Supercomputing Human Genome Cantor*, DR & Lim HA eds, World Scientific Pub. Co., Singapore, 47–59 (1991); Drmanac et al., *Science*, 260, 1649–1652 (1993); Lehrach et al., *Genome Analysis: Genetic and Physical Mapping*, 1, 39–81 (1990), Cold Spring Harbor Laboratory Press; Drmanac et al., *Nucl. Acids Res.*, 4691 (1986); Stevanovic et al., *Gene*, 79, 139 (1989); Panusku et al., *Mol. Biol. Evol.*, 1, 607 (1990); Nizetic et al., *Nucl. Acids Res.*, 19, 182 (1991); Drmanac et al., *J. Biomol. Struct. Dyn.*, 5, 1085 (1991); Hoheisel et al., *Mol. Gen.*, 4, 125–132 (1991); Strezoska et al., *Proc. Nat'l. Acad. Sci.* (USA), 88, 10089 (1991); Drmanac et al., *Nucl. Acids Res.*, 19, 5839 (1991); and Drmanac et al., *Int. J. Genome Res.*, 1, 59–79 (1992).

EXAMPLE 16

Determining Sequence from Hybridization Data

Sequence assembly may be interrupted where ever a given overlapping (N−1) mer is duplicated two or more times. Then either of the two N-mers differing in the last nucleotide may be used in extending the sequence. This branching point limits unambiguous assembly of sequence.

Reassembling the sequence of known oligonucleotides that hybridize to the target nucleic acid to generate the complete sequence of the target nucleic acid may not be accomplished in some cases. This is because some information may be lost if the target nucleic acid is not in fragments of appropriate size in relation to the size of oligonucleotide that is used for hybridizing. The quantity of information lost is proportional to the length of a target being sequenced. However, if sufficiently short targets are used, their sequence msy be unambiguously determined.

The probable frequency of duplicated sequences that would interfere with sequence assembly which is distributed along a certain length of DNA may be calculated. This derivation requires the introduction of the definition of a parameter having to do with sequence organization: the sequence subfragment (SF). A sequence subfragment results if any part of the sequence of a target nucleic acid starts and ends with an (N−1)mer that is repeated two or more times within the target sequence. Thus, subfragments are sequences generated between two points of branching in the process of assembly of the sequences in the method of the invention. The sum of all subfragments is longer than the actual target nucleic acid because of overlapping short ends. Generally, subfragments may not be assembled in a linear order without additional information since they have shared (N−1)mers at their ends and starts. Different numbers of subfragments are obtained for each nucleic acid target depending on the number of its repeated (N−1) mers. The number depends on the value of N−1 and the length of the target.

Probability calculations can estimate the interrelationship of the two factors. If the ordering of positive N-mers is accomplished by using overlapping sequences of length N−1 or at an average distance of $A_o$, the N−1 of a fragment Lf bases long is given by equation one:

$$N_{sf}=1+A_o\times\Sigma K\times P(K, L_f)$$

Where K greater than or =2, and P (K, $L_f$) represents the probability of an N-mer occurring K-times on a fragment $L_f$ base long. Also, a computer program that is able to form subfragments from the content of N-mers for any given sequence is described below in Example 18.

The number of subfragments increases with the increase of lengths of fragments for a given length of probe. Obtained subfragments may not be uniquely ordered among themselves. Although not complete, this information is very useful for comparative sequence analysis and the recognition of functional sequence characteristics. This type of information may be called partial sequence. Another way of obtaining partial sequence is the use of only a subset of oligonucleotide probes of a given length.

There may be relatively good agreement between predicted sequence according to theory and a computer simulation for a random DNA sequence. For instance, for N−1=7, [using an 8-mer or groups of sixteen 10-mers of type 5' (A,T,C,G) $B_8$ (A,T,C,G) 3'] a target nucleic acid of 200 bases will have an average of three subfragments. However, because of the dispersion around the mean, a library of target nucleic acid should have inserts of 500 bp so that less than 1 in 2000 targets have more than three subfragments. Thus, in an ideal case of sequence determination of a long nucleic acid of random sequence, a representative library with sufficiently short inserts of target nucleic acid may be used. For such inserts, it is possible to reconstruct the individual target by the method of the invention. The entire sequence of a large nucleic acid is then obtained by overlapping of the defined individual insert sequences.

To reduce the need for very short fragments, e.g. 50 bases for 8-mer probes. The information contained in the overlapped fragments present in every random DNA fragmentation process like cloning, or random PCR is used. It is also possible to use pools of short physical nucleic acid fragments. Using 8-mers or 11-mers like 5' (A, T, C, G) $N_8$ (A, T, C ,G )3' for sequencing 1 megabase, instead of needing 20,000 50 bp fragments only 2,100 samples are sufficient. This number consists of 700 random 7 kb clones (basic library), 1250 pools of 20 clones of 500 bp (subfragments ordering library) and 150 clones from jumping (or similar) library. The developed algorithm (see Example 18) regenerates sequence using hybridization data of th these described samples.

EXAMPLE 17

Hybridization With Oligonucleotides

Oligonucleotides were either purchased from Genosys Inc., Houston, Tex. or made on an Applied Biosystems 381A DNA synthesizer. Most of the probes used were not purified by HPLC or gel electrophoresis. For example, probes were designed to have both a single perfectly complementary target in interferon, a M13 clone containing a 921 bp Eco RI-Bgl II human B1-interferon fragment (Ohno and Tangiuchi, Proc. Natl. Acad. Sci. 74: 4370–4374 (1981)], and at least one target with an end base mismatch in M13 vector itself.

End labelling of oligonucleotides was performed as described [Maniatis et al., *Molecular Cloning: A Laboratory Manual*, Cold Spring Harbor Laboratory Cold Spring Harbor, New York (1982)] in 10 μl containing T4-polynucleotide kinase (5 units Amersham), $\gamma^{32P}$-ATP (3.3 pM, 10 μCi Amersham 3000 Ci/mM) and oligonucleotide (4 pM, 10 ng). Specific activities of the probes were 2.5–5×10 9 cpm/nM.

Single stranded DNA (2 to 4 μl in 0.5 NaOH, 1.5 M NaCl) was spotted on a Gene Screen membrane wetted with the same solution, the filters were neutralized in 0.05 M $Na_2HPO_4$ pH 6.5, baked in an oven at 80° C. for 60 min. and UV irradiated for 1 min. Then, the filters were incubated in hybridization solution (0.5 M $Na_2HPO_4$ pH 7.2, 7% sodium lauroyl sarcosine for 5 min at room temperature and placed on the surface of a plastic Petri dish. A drop of hybridization solution (10 μl, 0.5 M $Na_2HPO_4$ pH 7.2, 7% sodium lauroyl sarcosine) with a $^{32}p$ end labelled oligomer probe at 4 nM concentration was placed over 1–6 dots per filter, overlaid with a square piece of polyethylene (approximately 1×1 cm.), and incubated in a moist chamber at the indicated temperatures for 3 hr. Hybridization was stopped by placing the filter in 6×SSC washing solution for 3×5 minute at 0° C. to remove unhybridized probe. The filter was either dried, or further washed for the indicated times and temperatures, and autoradiographed. For discrimination measurements, the dots were excised from the dried filters after autoradiography [a phosphoimager (Molecular Dynamics, Sunnyvale, Calif.) may be used] placed in liquid scintillation cocktail and counted. The uncorrected ratio of cpms for IF and M13 dots is given as D.

The conditions reported herein allow hybridization with very short oligonucleotides but ensure discriminations between matched and mismatched oligonucleotides that are complementary to and therefore bind to a target nucleic acid. Factors which influence the efficient detection of hybridization of specific short sequences based on the degree of discriminations (D) between a perfectly complementary target and an imperfectly complementary target with a single mismatch in the hybrid are defined. In experimental tests, dot blot hybridization of twenty-eight probes that were 6 to 8 nucleotides in length to two M13 clones or to model oligonucleotides bound to membrane filters was accomplished. The principles guiding the experimental procedures are given below.

Oligonucleotide hybridization to filter bound target nucleic acids only a few nucleotides longer than the probe in conditions of probe excess is a pseudo-first order reaction with respect to target concentration. This reaction is defined by:

$$S_t/S_o=e^{-k_h[OP]t}$$

Wherein $S_t$ and $S_o$ are target sequence concentrations at time t and $t_0$, respectively. (OP) is probe concentration and t is temperature. The rate constant for hybrid formation, $k_h$ increases only slightly in the 0° C. to 30° C. range (Porschke and Eigen, *J. Mol. Biol.* 62: 361 (1971); Craig et al., *J. Mol. Biol.* 62: 383 (1971)]. Hybrid melting is a first order reaction with respect to hybrid concentration (here replaced by mass due to filter bound state) as shown in:

$$H_t/H_o = e^{-kmt}$$

In this equation, $H_t$ and $H_o$ are hybrid concentrations at times t and $t_o$, respectively; $k_m$ is a rate constant for hybrid melting which is dependent on temperature and salt concentration [Ikuta et al., *Nucl. Acids Res.* 15: 797 (1987); Porsclike and Eigen, *J. Mol. Biol.* 62: 361 (1971); Craig et al., J. Mol. Biol. 62: 303 (1971)]. During hybridization, which is a strand association process, the back, melting, or strand dissociation, reaction takes place as well. Thus, the amount of hybrid formed in time is result of forward and back reactions. The equilibrium may be moved towards hybrid formation by increasing probe concentration and/or decreasing temperature. However, during washing cycles in large volumes of buffer, the melting reaction is dominant and the back reaction hybridization is insignificant, since the probe is absent. This analysis indicates workable Short Oligonucleotide Hybridization (SOH) conditions call be varied for probe concentration or temperature.

D or discrimination is defined in equation four:

$$D = H_p(t_w)/H_i(t_w)$$

$H_p(t_w)$ and $H_i(t_w)$ are the amounts hybrids remaining after a washing time, $t_w$, for the identical amounts of perfectly and imperfectly complementary duplex, respectively. For a given temperature, the discrimination D changes with the length of washing time and reaches the maximal value when $H_i = B$ which is equation five.

The background, B, represents the lowest hybridization signal detectable in the system. Since any further decrease of $H_i$ may not be examined, D increases upon continued washing. Washing past $t_w$ just decreases $H_p$ relative to B, and is seen as a decrease in D. The optimal washing time, $t_w$, for imperfect hybrids, from equation three and equation five is:

$$t_w W = -ln(B/H_i(t_0))/k_{m,i}$$

Since $H_p$ is being washed for the same $t_w$, combining equations, one obtains the optimal discrimination function:

$$D = e^{ln(B/Hi(t0))km,p/km,i} \times H_p(t_0)/B$$

The change of D as a function, of T is important because of the choice of an optimal washing temperature. It is obtained by substituting the Arhenius equation which is:

$$K = Ae^{-E\alpha/RT}$$

into the previous equation to form the final equation:

$$D = H_p((t_0)/B \times (B/H_i(t_0))^{(Ap/Ai)} e^{(E_{\alpha,i}-E_{\alpha,p})/RT};$$

Wherein B is less than $H_i$ (to)

Since the activation energy for perfect hybrids, $E_{\alpha,p}$, and the activation energy for imperfect hybrids, $E_{\alpha,i}$, can be either equal, or $E_{\alpha,i}$ less than $E_{\alpha,p}$ D is temperature independent, or decreases with increasing temperature, respectively. This result implies that the search for stringent temperature conditions for good discrimination in SOH is unjustified. By washing at lower temperatures, one obtains equal or better discrimination, but the time of washing exponentially increases with the decrease of temperature. Discrimination more strongly decreases with T, if $H_i(t_o)$ increases relative to $H_p(t_0)$.

D at lower temperatures depends to a higher degree on the $H_p(t_0)/B$ ratio than on the $H_p(t_0)/H_i(t_0)$ ratio. This result indicates that it is better to obtain a sufficient quantity of $H_p$ in the hybridization regardless of the discrimination that can be achieved in this step. Better discrimination can then be obtained by washing, since the higher amounts of perfect hybrid allow more time for differential melting to show an effect. Similarly, using larger amounts of target nucleic acid a necessary discrimination can be obtained even with small differences between $K_{m,p}$ and $K_{m,i}$.

Extrapolated to a more complex situation than covered in this simple model, the result is that washing at lower temperatures is even more important for obtaining discrimination in the case of hybridization of a probe having many end-mismatches within a given nucleic acid target.

Using the described theoretical principles as a guide for experiments, reliable hybridizations have been obtained with probes six to eight nucleotides in length. All experiments were performed with a floating plastic sheet providing a film of hybridization solution above the filter. This procedure allows maximal reduction in the amount of probe, and thus reduced label costs in dot blot hybridizations. The high concentration of sodium lauroyl sarcosine instead of sodium lauroyl sulfate in the phosphate hybridization buffer allows dropping the reaction from room temperature down to 12° C. Similarly, the 4–6×SSC, 10% sodium lauroyl sarcosine buffer allows hybridization at temperatures as low as 2° C. The detergent in these buffers is for obtaining tolerable background with up to 40 nM concentrations of labelled probe. Preliminary characterization of the thermal stability of short oligonucleotide hybrids was determined on a prototype octamer with 50% G+C content, i.e. probe of sequence TGCTCATG. The theoretical expectation is that this probe is among the less stable octamers. Its transition enthalpy is similar to those of more stable heptamers or, even to probes 6 nucleotides in length (Bresslauer et al., *Proc. Natl. Acad. Sci.* U.S.A. 83: 3746 (1986)). Parameter $T_d$, the temperature at which 50% of the hybrid is melted in unit time of a minute is 18° C. The result shows that $T_d$ is 15° C. lower for the 8 bp hybrid than for an 11 bp duplex [Wallace et al., *Nucleic Acids Res.* 6: 3543 (1979)].

In addition to experiments with model oligonucleotides, an M13 vector was chosen as a system for a practical demonstration of short oligonucleotide hybridization. The main aim was to show useful end-mismatch discrimination with a target similar to the ones which will be used in various applications of the method of the invention. Oligonucleotide probes for the M13 model were chosen in such a way that the M13 vector itself contains the end mismatched base. Vector IF, an M13 recombinant containing a 921 bp human interferon gene insert, carries single perfectly matched target. Thus, IF has either the identical or a higher number of mismatched targets in comparison to the M13 vector itself.

Using low temperature conditions and dot blots, sufficient differences in hybridization signals were obtained between tie dot containing the perfect and the mismatched targets and the dot containing the mismatched targets only. This was true for the 6-mer oligonucleotides and was also true for the 7 and 8-mer oligonucleotides hybridized to the large IF-M13 pair of nucleic acids.

The hybridization signal depends on the amount of target available on the filter for reaction with the probe. A necessary control is to show that the difference in sign intensity is not a reflection of varying amounts of nucleic acid in the two dots. Hybridization with a probe that has the same number and kind of targets in both IF and M13 shows that there is an equal amount of DNA in the dots. Since the efficiency of hybrid formation increases with hybrid length, the signal for a duplex having six nucleotides was best detected with a high mass of oligonucleotide target bound to the filter. Due to their lower molecular weight, a larger number of oligonucleotide target molecules can be bound to a given surface area when compared to large molecules of nucleic acid that serves as target.

To measure the sensitivity of detection with unpurified DNA, various amounts of phage supernatants were spotted on the filter and hybridized with a 32 P-labelled octamer. As little as 50 million unpurified phage containing no more than 0.5 ng of DNA gave a detectable signal indicating that sensitivity of the short oligonucleotide hybridization method is sufficient. Reaction time is short, adding to the practicality.

As mentioned in the theoretical section above, the equilibrium yield of hybrid depends oil probe concentration and/or temperature of reaction. For instance, the signal level for the same amount of target with 4 nM octamer at 13° C. is 3 times lower than with a probe concentration of 40 nM, and is decreased 4.5-times by raising the hybridization temperature to 25° C.

The utility of the low temperature wash for achieving maximal discrimination is demonstrated. To make the phenomenon visually obvious, 50 times more DNA was put in the M13 dot than in the IF dot using hybridization with a vector specific probe. In this way, the signal after the hybridization step with the actual probe was made stronger in the, mismatched that in the matched case. The $H_p/H_i$ ratio was 1:4. Inversion of signal intensities after prolonged washing at 7° C. was achieved without a massive loss of perfect hybrid, resulting in a ratio of 2:1. In contrast, it is impossible to achieve any discrimination at 25° C., since the matched target signal is already brought down to the background level with 2 minute washing; at the same time, the signal from the mismatched hybrid is still detectable. The loss of discrimination at 13° C. compared to 7° C. is not so great but is clearly visible. If one considers the 90 minute point at 7° C. and the 15 minute point at 13° C. when, the mismatched hybrid signal is near the background level, which represents optimal washing times for the respective conditions, it is obvious that the amount of several times greater at 7° C. than at 13° C. To illustrate this further, the time course of the change discrimination with washing of the same amount of starting hybrid at the two temperatures shows the higher maximal D at the lower temperature. These results confirm the trend in the change of D with temperature and the ratio of amounts of the two types of hybrid at the start of the washing step.

In order to show the general utility of the short oligonucleotide hybridization conditions, we have looked hybridization of 4 heptamers, 10 octamers and an additional 14 probes up to 12 nucleotides in length in our simple M13 system. These include-the nonamer GTTTTTTAA and octamer GGCAGGCG representing the two extremes of GC content. Although GC content and sequence are expected to influence the stability of short hybrids [Bresslauer et al., *Proc. Natl. Acad. Sci. U.S.A.* 83: 3746 (1986)], the low temperature short oligonucleotide conditions were applicable to all tested probes in achieving sufficient discrimination. Since the best discrimination value obtained with probes 13 nucleotides in length was 20, a several fold drop due to sequence variation is easily tolerated.

The M13 system has the advantage of showing the effects of target DNA complexity on the levels of discrimination. For two octamers having either none or five mismatched targets and differing in only one GC pair the observed discriminations were 18.3 and 1.7, respectively.

In order to show the utility of this method, three probes 8 nucleotides in length were tested on a collection of 51 plasmid DNA dots made from a library in Bluescript vector. One probe was present and specific for Bluescript vector but was absent in M13, while the other two probes had targets that were inserts of known sequence. This system allowed the use of hybridization negative or positive control DNAs with each probe. This probe sequence (CTCCCTTT) also had a complementary target in the interferon insert. Since the M13 dot is negative while the interferon insert in either M13 or Bluescript was positive, the hybridization is sequence specific. Similarly, probes that detect the target sequence in only one of 51 inserts, or in none of the examined inserts along with controls that confirm that hybridization would have occurred if the appropriate targets were present in the clones.

Thermal stability curves for very short oligonucleotide hybrids that are 6–8 nucleotides in length are at least 15° C. lower than for hybrids 11–12 nucleotides in length [FIG. 1 and Wallace et al., *Nucleic Acids Res.* 6: 3543–3557 (1979)]. However, performing the hybridization reaction at a low temperature and with a very practical 0.4–40 nM concentration of oligonucleotide probe allows the detection of complementary sequence in a known or unknown nucleic acid target. To determine an unknown nucleic acid sequence completely, an entire set containing 65,535 8-mer probes may be used. Sufficient amounts of nucleic acid for this purpose are present in convenient biological samples such as a few microliters of M13 culture, a plasmid prep from 10 ml of bacterial culture or a single colony of bacteria, or less than 1 $\mu$l of a standard PCR reaction.

Short oligonucleotides 6–10 nucleotides long give excellent discrimination. The relative decrease in hybrid stability with a single end mismatch is greater than for longer probes. Results with the octamer TGCTCATG support this conclusion. In the experiments, the target with a G/T end mismatch, hybridization to the target of this type of mismatch is the most stable of all other types of oligonucleotide. This discrimination achieved is the same as or greater than an internal G/T mismatch in a 19 base paired duplex greater than an internal G/T mismatch in a 19 paired duplex [Ikuta et al., Nucl. Acids res. 15: 797 (1987)]. Exploiting these discrimination properties using the described hybridization conditions for short oligonucleotide hybridization allows a very precise determination of oligonucleotide targets.

In contrast to the ease of detecting discrimination between perfect and imperfect hybrids, a problem that may exist with using very short oligonucleotides is the preparation of sufficient amounts of hybrids. In practice, the need to discriminate $H_p$ and $H_i$ is aided by increasing the amount of DNA in the dot and/or the probe concentration, or by decreasing the hybridization temperature. However, higher probe concentrations usually increase background. Moreover, there are limits to the amounts of target nucleic acid that are practical to use. This problems was solved by the higher concentration of the detergent Sarcosyl which gave an effective background with 4 nM of probe. Further improvements may be effected either in the use of competitors for unspecific binding of probe to filter, or by changing the hybridization support material. Moreover, for probes having $E_\alpha$ less than 45 Kcal/mol (e.g. for many heptamers and a majority of hexamers, modified oligonucleotides give a more stable hybrid [Asseline, et al., *Proc. Nat'l Acad. Sci.* 81: 3297 (1984)] than their unmodified counterparts. The hybridization conditions described in this invention for short oligonucleotide hybridization using low temperatures give better discriminating for all sequences and duplex hybrid inputs. The only price paid in achieving uniformity in hybridization conditions for different sequences is an increase in washing time from minutes to up to 24 hours depending on the sequence. Moreover, the washing time can be further reduced by decreasing the salt concentration.

Although there is excellent discrimination of one matched hybrid over a mismatched hybrids, in short oligonucleotide hybridization, signals from mismatched hybrids exist, with the majority of the mismatch hybrids resulting from end mismatch. This may limit insert sizes that may be effectively examined by a probe of a certain length.

The influence of sequence complexity on discrimination cannot be ignored. However, the complexity effects are more significant when defining sequence information by short oligonucleotide hybridization for specific, nonrandom sequences, and can be overcome by using an appropriate probe to target length ratio. The length ratio is chosen to make unlikely, on statistical grounds, the occurrence of specific sequences which have a number of end-mismatches which would be able to eliminate or falsely invert discrimination. Results suggest the use of oligonucleotides 6, 7, and 8 nucleotides in length on target nucleic acid inserts shorter than 0.6, 2.5, and 10 kb, respectively.

EXAMPLE 18

Sequencing a Target Using Octamers and Nonamers

In this example, hybridization conditions that were used are described supra in Example 17. Data resulting from the hybridization of octamer and nonamer oligonucleotides shows that sequencing by hybridization provides an extremely high degree of accuracy. In this experiment, a known sequence was used to predict a series of contiguous overlapping component octamer and nonamer oligonucleotides.

In addition to the perfectly matching oligonucleotides, mismatch oligonucleotides, mismatch oligonucleotides wherein internal or end mismatches occur in the duplex formed by the oligonucleotide and the target were examined. In these analyses, the lowest practical temperature was used to maximize hybridization formation. Washes were accomplished at the same or lower temperatures to ensure maximal discrimination by utilizing the greater dissociation rate of mismatch versus matched oligonucleotide/target hybridization. These conditions are shown to be applicable to all sequences although the absolute hybridization yield is shown to be sequence dependent.

The least destabilizing mismatch that can be postulated is a simple end mismatch, so that the test of sequencing by hybridization is the ability to discriminate perfectly matched oligonucleotide/target duplexes from end-mismatched oligonucleotide/target duplexes.

The discriminative values for 102 of 105 hybridizing oligonucleotides in a dot blot format were greater than 2 allowing a highly accurate generation of the sequence. This system also allowed an analysis of the effect of sequence on hybridization formation and hybridization instability.

One hundred base pairs of a known portion of a human β-interferon genes prepared by PCR, i.e. a 100 bp target sequence, was generated with data resulting from the hybridization of 105 oligonucleotides probes of known sequence to the target nucleic acid. The oligonucleotide probes used included 72 octamer and 21 nonamer oligonucleotides whose sequence was perfectly complementary to the target. The set of 93 probes provided consecutive overlapping frames of the target sequence e displaced by one or two bases.

To evaluate the effect of mismatches, hybridization was examined for 12 additional probes that contained at least one end mismatch when hybridized to the 100 bp test target sequence. Also tested was the hybridization of twelve probes with target end-mismatched to four other control nucleic acid sequences chosen so that the 12 oligonucleotides formed perfectly matched duplex hybrids with the four control DNAs. Thus, the hybridization of internal mismatched, end-mismatched and perfectly matched duplex pairs of oligonucleotide and target were evaluated for each oligonucleotide used in the experiment. The effect of absolute DNA target concentration on the hybridization with the test octamer and nonamer oligonucleotides was determined by defining target DNA concentration by detecting hybridization of a different oligonucleotide probe to a single occurrence non-target site within the co-amplified plasmid DNA.

The results of this experiment showed that all oligonucleotides containing perfect matching complementary sequence to the target or control DNA hybridized more strongly than those oligonucleotides having mismatches. To come to this conclusion, we examined $H_p$ and D values for each probe. $H_p$ defines the amount of hybrid duplex formed between a test target and an oligonucleotide probe. By assigning values of between 0 and 10 to the hybridization obtained for the 105 probes, it was apparent that 68.5% of the 105 probes had an $H_p$ greater than 2.

Discrimination (D) values were obtained where D was defined as the ratio of signal intensities between 1) the dot containing a perfect matched duplex formed between test oligonucleotide and target or control nucleic acid and 2) the dot containing a mismatch duplex formed between the same oligonucleotide and a different site within the target or control nucleic acid. Variations in the value of D result from either 1) perturbations in the hybridization efficiency which allows visualization of signal over background, or 2) the type of mismatch found between the test oligonucleotide and the target. The D values obtained in this experiment were between 2 and 40 for 102 of the 105 oligonucleotide probes examined. Calculations of D for the group of 102 oligonucleotides as a whole showed the average D was 10.6.

There were 20 cases where oligonucleotide/target duplexes exhibited an end-mismatch. In five of these, D was greater than 10. The large D value in these cases is most likely due to hybridization destabilization caused by other than the most stable (G/T and G/A) end mismatches. The other possibility is there was an error in the sequence of either the oligonucleotides or the target.

Error in the target for probes with low $H_p$ was excluded as a possibility because such an error would have affected the hybridization of each of the other eight overlapping oligonucleotides. There was no apparent instability due to sequence mismatch for the other overlapping oligonucleotides, indicating the target sequence was correct. Error in the oligonucleotide sequence was excluded as a possibility after the hybridization of seven newly synthesized oligonucleotides was re-examined. Only 1 of the seven oligonucleotides resulted in a better D value. Low hybrid formation values may result from hybrid instability or from an inability to form hybrid duplex. An inability to form hybrid duplexes would result from either 1) self complementarity of the chosen probe or 2) target/target self hybridization. Oligonucleotide/oligonucleotide duplex formation may be favored over oligonucleotide/target hybrid duplex formation if the probe was self-complementary. Similarly, target/target association may be favored if the target was self-complementary or may form internal palindromes. In evaluating these possibilities, it was apparent from probe analysis that the questionable probes did not form hybrids with themselves. Moreover, in examining the contribution of target/target hybridization, it was determined that one of the questionable oligonucleotide probes hybridized inefficiently with two different DNAs containing the same target. The low probability that two different DNAs have a self-complementary region for the same target sequence leads to the conclusion that target/target hybridization did not contribute to low hybridization formation. Thus, these results indicate that hybrid instability and not the inability to form hybrids was the cause of the low hybrid formation observed for specific oligonucleotides. The results also indicate that low hybrid formation is due to the specific sequences of certain oligonucleotides. Moreover, the results indicate that reliable results may be obtained to generate sequences if octamer and nonamer oligonucleotides are used.

These results show that using the methods described long sequences of any specific target nucleic acid may be generated by maximal and unique overlap of constituent oligonucleotides. Such sequencing methods are dependent on the content of the individual component oligomers regardless of their frequency and their position.

The sequence which is generated using the algorithm described below is of high fidelity. The algorithm tolerates false positive signals from the hybridization dots as is indicated from the fact the sequence generated from the 105 hybridization values, which included four less reliable values, was correct. This fidelity in sequencing by hybridization is due to the "all or none" kinetics of short oligonucleotide hybridization and the difference in duplex stability that exists between perfectly matched duplexes and mismatched duplexes. The ratio of duplex stability of matched and end-mismatched duplexes increases with decreasing duplex length. Moreover, binding energy decreases with decreasing duplex length resulting in a lower hybridization efficiency. However, the results provided show that octamer hybridization allows the balancing of the factors affecting duplex stability and discrimination to produce a highly accurate method of sequencing by hybridization. Results presented in other examples show that oligonucleotides that are 6, 7, or 8 nucleotides can be effectively used to generate reliable sequence on targets that are 0.5 kb (for hexamers) 2 kb (for septamers) and 6 kb (for octamers). The sequence of long fragments may be overlapped to generate a complete genome sequence.

An algorithm to determine sequence by hybridization is described in Example 18.

EXAMPLE 19

Algorithm

This example describes an algorithm for generation of a long sequence written in a four letter alphabet from constituent k-tuple words in a minimal number of separate, randomly defined fragments of a starting nucleic acid sequence where K is the length of an oligonucleotide probe. The algorithm is primarily intended for use in the sequencing by hybridization (SBH) process. The algorithm is based on subfragments (SF), informative fragments (IF) and the possibility of using pools of physical nucleic sequences for defining informative fragments.

As described, subfragments may be caused by branch points in the assembly process resulting from the repetition of a K–1 oligomer sequence in a target nucleic acid. Subfragments are sequence fragments found between any two repetitive words of the length K–1 that occur in a sequence. Multiple occurrences of K–1 words are the cause of interruption of ordering the overlap of K-words in the process of sequence generation. Interruption leads to a sequence remaining in the form of subfragments. Thus, the unambiguous segments between branching points whose order is not uniquely determined are called sequence subfragments.

Informative fragments are defined as fragments of a sequence that are determined by the nearest ends of overlapped physical sequence fragments.

A certain number of physical fragments may be pooled without losing the possibility of defining informative fragments. The total length of randomly pooled fragments depends on the length of k-tuples that are used in the sequencing process.

The algorithm consists of two main units. The first part is used for generation of subfragments from the set of k-tuples contained in a sequence. Subfragments may be generated within the coding region of physical nucleic acid sequence of certain sizes, or within the informative fragments defined within long nucleic acid sequences. Both types of fragments are members of the basic library. This algorithm does not describe the determination of the content of the k-tuples of the informative fragments of the basic library, i.e. the step of preparation of informative fragments to be used in the sequence generation process.

The second part of the algorithm determines the linear order of obtained subfragments with the purpose of regenerating the complete sequence of the nucleic acid fragments of the basic library. For this purpose a second, ordering library is used, made of randomly pooled fragments of the starting sequence. The algorithm does not include the step of combining sequences of basic fragments to regenerate an entire, megabase plus sequence. This may be accomplished using the link-up of fragments of the basic library which is a prerequisite for informative fragment generation. Alternatively, it may be accomplished after generation of sequences of fragments of the basic library by this algorithm, using search for their overlap, based on the presence of common end-sequences.

The algorithm requires neither knowledge of the number of appearances of a given k-tuple in a nucleic acid sequence of the basic and ordering libraries, nor does it require the information of which k-tuple words are present on the ends of a fragment. The algorithm operates with the mixed content of k-tuples of various length. The concept of the algorithm enables operations with the k-tuple sets that contain false positive and false negative k-tuples. only in specific cases does the content of the false k-tuples primarily influence the completeness and correctness of the generated sequence. The algorithm may be used for optimization of parameters in simulation experiments, as well as for sequence generation in the actual SBH experiments e.g. generation of the genomic DNA sequence. In optimization of parameters, the choice of the oligonucleotide probes (k-tuples) for practical and convenient fragments and/or the choice of the optimal lengths and the number of fragments for the defined probes are especially important.

This part of the algorithm has a central role in the process of the generation of the sequence from the content of k-tuples. It is based on the unique ordering of k-tuples by means of maximal overlap. The main obstacles in sequence generation are specific repeated sequences and false positive and/or negative k-tuples. The aim of this part of the algorithm is to obtain the minimal number of the longest possible subfragments, with correct sequence. This part of the algorithm consists of one basic, and several control steps. A two-stage process is necessary since certain information can be used only after generation of all primary subfragments.

The main problem of sequence generation is obtaining a repeated sequence from word contents that by definition do not carry information on the number of occurrences of the particular k-tuples. The concept of the entire algorithm depends on the basis on which this problem is solved. In principle, there are two opposite approaches: 1) repeated sequences may be obtained at the beginning, in the process of generation of pSFs, or 2) repeated sequences can be obtained later, in the process of the final ordering of the subfragments. In the first case, pSFs contain an excess of sequences and in the second case, they contain a deficit of sequences. The first approach requires elimination of the excess sequences generated, and the second requires permitting multiple use of some of the subfragments in the process of the final assembling of the sequence.

The difference in the two approaches in the degree of strictness of the rule of unique overlap of k-tuples. The less severe rule is: k-tuple X is unambiguously maximally overlapped with k-tuple Y if and only if, the rightmost k−1 end of k-tuple X is present only on the leftmost end of k-tuple Y. This rule allows the generation of repetitive sequences and the formation of surplus sequences.

A stricter rule which is used in the second approach has an addition caveat: k-tuple X is unambiguously maximally overlapped with k-tuple Y if and only if, the rightmost K−1 end of k-tuple X is present only on the leftmost end of k-tuple Y and if the leftmost K−1 end of k-tuple Y is not present on the rightmost end of any other k-tuple. The algorithm based on the stricter rule is simpler, and is described herein.

The process of elongation of a given subfragment is stopped when the right k−1 end of the last k-tuple included is not present on the left end of any k-tuple or is present on two or more k-tuples. If it is present on only one k-tuple the second part of the rule is tested. If in addition there is a k-tuple which differs from the previously included one, the assembly of the given subfragment is terminated only on the first leftmost position. If this additional k-tuple does not exist, the conditions are met for unique k−1 overlap and a given subfragment is extended to the right by one element.

Beside the basic rule, a supplementary one is used to allow the usage of k-tuples of different lengths. The maximal overlap is the length of k−1 of the shorter k-tuple of the overlapping pair. Generation of the pSFs is performed starting from the first k-tuple from the file in which k-tuples are displayed randomly and independently from their order in a nucleic acid sequence. Thus, the first k-tuple in the file is not necessarily on the beginning of the sequence, nor on the start of the particular subfragment. The process of subfragment generation is performed by ordering the k-tuples by means of unique overlap, which is defined by the described rule. Each used k-tuple is erased from the file. At the point when there are no further k-tuples unambiguously overlapping with the last one included, the building of subfragment is terminated and the buildup of another pSF is started. Since generation of a majority of subfragments does not begin from their actual starts, the formed pSF are added to the k-tuple file and are considered as a longer k-tuple. Another possibility is to form subfragments going in both directions from the starting k-tuple. The process ends when further overlap, i.e. the extension of any of the subfragments, is not possible.

The pSFs can be divided in three groups: 1) Subfragments of the maximal length and correct sequence in cases of exact k-tuple set; 2) short subfragments, formed due to the used of the maximal and unambiguous overlap rule on the incomplete set, and/or the set with some false positive k-tuples; and 3) pSFs of an incorrect sequence. The incompleteness of the set in 2) is caused by false negative results of a hybridization experiment, as well as by using an incorrect set of k-tuples. These are formed due to the false positive and false negative k-tuples and can be: a) misconnected subfragments; b) subfragments with the wrong end; and c) false positive k-tuples which appears as false minimal subfragments.

Considering false positive k-tuples, there is the possibility for the presence of a k-tuple containing more than one wrong base or containing one wrong base somewhere in the middle, as well as the possibility for a k-tuple with a wrong base on the end. Generation of short, erroneous or misconnected subfragments is caused by the latter k-tuples. The k-tuples of the former two kinds represent wrong pSFs with length equal to k-tuple length.

In the case of one false negative k-tuple, pSFs are generated because of the impossibility of maximal overlapping. In the case of the presence of one false positive k-tuple with the wrong base on its leftmost or rightmost end, pSFs are generated because of the impossibility of unambiguous overlapping. When both false positive and false negative k-tuples with a common k−1 sequence are present in the file, pSFs are generated, and one of these pSFs contains the wrong k-tuple at the relevant end.

The process of correcting subfragments with errors in sequence and the linking of unambiguously connected pSF is performed after subfragment generation and in the process of subfragment ordering. The first step which consists of cutting the misconnected pSFs and obtaining the final subfragments by unambiguous connection of pSFs is described below.

There are two approaches for the formation of misconnected subfragments. In the first a mistake occurs when an erroneous k-tuple appears on the points of assembly of the repeated sequences of lengths k−1. In the second, the repeated sequences are shorter than k−1. These situations can occur in two variants each. In the first variant, one of the repeated sequences represents the end of a fragment. In the second variant, the repeated sequence occurs at any position within the fragment. For the first possibility, the absence of some k-tuples from the file (false negatives) is required to generate a misconnection. The second possibility requires the presence of both false negative and false positive k-tuples in the file. Considering the repetitions of k−1 sequence, the lack of only one k-tuple is sufficient when either end is repeated internally. The lack of two is needed for strictly internal repetition. The reason is that the end of a sequence can be considered informatically as an endless linear array of false negative k-tuples. From the "smaller than k−1 case", only the repeated sequence of the length of k−2, which requires two or three specific erroneous k-tuples, will be considered. It is very likely that these will be the only cases which will be detected in a real experiment, the others being much less frequent.

Recognition of the misconnected subfragments is more strictly defined when a repeated sequence does not appear at the end of the fragment. In this situation, one can detect further two subfragments, one of which contains on its leftmost, and the other on its rightmost end k−2 sequences which are also present in the misconnected subfragment. When the repeated sequence is on the end of the fragment, there is only one subfragment which contains k−2 sequence causing the mistake in subfragment formation on its leftmost or rightmost end.

The removal of misconnected subframents by their cutting is performed according to the common rule: If the leftmost or rightmost sequence of the length of k−2 of any subfragments is present in any other subfragment, the subfragment is to be cut into two subfragments, each of them containing k−2 sequence. This rule does not cover rarer situations of a repeated end when there are more than one false negative k-tuple on the point of repeated k−1 sequence. Misconnected subfragments of this kind can be recognized by using the information from the overlapped fragments, or informative fragments of both the basic and ordering libraries. In addition, the misconnected subfragment will remain when two or more false negative k-tuples occur on both positions which contain the identical k−1 sequence. This is a very rare situation since it requires at least 4 specific false k-tuples. An additional rule can be introduced to cut these subfragments on sequences of length k if the given sequence can be obtained by combination of sequences shorter than k−2 from the end of one subfragment and the start of another.

By strict application of the described rule, some completeness is lost to ensure the accuracy of the output. Some of the subfragments will be cut although they are not misconnected since they fit into the pattern of a misconnected subfragment. There are several situations of this kind. For example, a fragment, beside at least two identical k−1 sequences, contains any k−2 sequence from k−1 or a fragment contains k−2 sequence repeated at least twice and at least one false negative k-tuple containing given k−2 sequence in the middle, etc. The aim of this part of the algorithm is to reduce the number of pSFs to a minimal number of longer subfragments with correct sequence. The generation of unique longer subfragments or a complete sequence is possible in two situations. The first situation concerns the specific order of repeated k−1 words. There are cases in which some or all maximally extended pSFs (the first group of pSFs) can be uniquely ordered. For example, in fragment S-R1-a-R2-b-R1-c-R2-E where S and E are the start and end of a fragment, a, b , and c are different sequences specific to respective subfragments and R1 and R2 are two k−1 sequences that are tandemly repeated, five subfragments are generated (S-R1, R1-a-R2, R2-b-R1, R1-c-R2, and R-E). They may be ordered in two ways; the original sequence above or S-R1-c-R-b-R1-a-R-E. In contrast, in a fragment with the same number and types of repeated sequences but ordered differently, i.e. S-R1-a-R1-b-R-c-R-E, there is no other sequence which includes all subfragments. Examples of this type can be recognized only after the process of generation of pSFs. They represent the necessity for two steps in the process of pSF generation. The second situation of generation of false short subfragments on positions of nonrepeated k−1 sequences when the files contain false negative and/or positive k-tuples is more important.

The solution for both pSF groups consists of two parts. First, the false positive k-tuples appearing as the nonexisting minimal subfragments are eliminated. All k-tuple subfragments of length k which do not have an overlap on either end, of the length of longer than k-a on one end and longer than k-b on the other end, are eliminated to enable formation of the maximal number of connections. In our experiments, the values for a and b of 2 and 3, respectively, appeared to be adequate to eliminate a sufficient number of false positive k-tuples.

The merging of subfragments that can be uniquely connected is accomplished in the second step. The rule for connection is: two subfragments may be unambiguously connected if, and only if, the overlapping sequence at the relevant end or start of two subfragments is not present at the start and/or end of any other subfragment.

The exception is if one subfragment from the considered pair has the identical beginning and end. In that case connection is permitted, even if there is another subfragment with the same end present in the file. The main problem here is the precise definition of overlapping sequence. The connection is not permitted if the overlapping sequence unique for only one pair of subfragments is shorter than k−2, of it is k−2 or longer but an additional subfragment exists with the overlapping sequence of any length longer than k−4. Also, both the canonical ends of pSFs and the ends after omitting one (or few) last bases are considered as the overlapping sequences.

After this step some false positive k-tuples (as minimal subfragments) and some subfragments with a wrong end may survive. In addition, in very rare occasions where a certain number of some specific false k-tuples are simultaneously present, an erroneous connection may take place. These cases will be detected and solved in the subfragment ordering process, and in the additional control steps along with the handling of uncut "misconnected" subfragments.

The short subfragments that are obtained are of two kinds. In the common case, these subfragments may be unambiguously connected among themselves because of the distribution of repeated k−1 sequences. This may be done after the process of generation of pSFs and is a good example of the necessity for two steps in the process of pSF generation. In the case of using the file containing false positive and/or false negative k-tuples, short pSFs are obtained on the sites of nonrepeated k−1 sequences. Considering false positive k-tuples, a k-tuple may contain more than one wrong base (or containing one wrong base somewhere in the middle), as well as k-tuple on the end. Generation of short and erroneous (or misconnected) subfragments is caused by the latter k-tuples. The k-tuples of the former kind represent wrong pSFs with length equal to k-tuple length.

The aim of merging pSF part of the algorithm is the reduction of the number of pSFS to the minimal number of longer subfragments with the correct sequence. All k-tuple subfragments that do not have an overlap on either end, of the length of longer than k-a on one, and longer than k-b on the other end, are eliminated to enable the maximal number of connections. In this way, the majority of false positive k-tuples are discarded. The rule for connection is: two subfragments can be unambiguously connected if, and only if the overlapping sequence of the relevant end or start of two subfragments is not present on the start and/or end of any other subfragment. The exception is a subfragment with the identical beginning and end. In that case connection is permitted, provided that there is another subfragment with the same end present in the file. The main problem here is of precise definition of overlapping sequence. The presence of at least two specific false negative k-tuples on the points of repetition of k−1 or k−2 sequences, as well as combining of the false positive and false negative k-tuples may destroy or "mask" some overlapping sequences and can produce an unambiguous, but wrong connection of pSFs. To prevent this, completeness must be sacrificed on account of exactness: the connection is not permitted on the end-sequences shorter than k−2, and in the presence of an extra overlapping sequence longer than k−4. The overlapping sequences are defined from the end of the pSFs, or omitting one, or few last bases.

In the very rare situations, with the presence of a certain number of some specific false positive and false negative k-tuples, some subfragments with the wrong end can survive, some false positive k-tuples (as minimal subfragments) can remain, or the erroneous connection can take place. These cases are detected and solved in the subfragments ordering process, and in the additional control steps along with the handling of uncut, misconnected subfragments.

The process of ordering of subfragments is similar to the process of their generation. If one considers subfragments as longer k-tuples, ordering is performed by their unambiguous connection via overlapping ends. The informational basis for unambiguous connection is the division of subfragments generated in fragments of the basic library into groups representing segments of those fragments. The method is analogous to the biochemical solution of this problem based on hybridization with longer oligonucleotides with relevant connecting sequence. The connecting sequences are generated as subfragments using the k-tuple sets of the appropriate segments of basic library fragments. Relevant segments are defined by the fragments of the ordering library that overlap with the respective fragments of the basic library. The shortest segments are informative fragments of the ordering library. The longer ones are several neighboring informative fragments or total overlapping portions of fragments corresponding of the ordering and basic libraries. In order to decrease the number of separate samples, fragments of the ordering library are randomly pooled, and the unique k-tuple content is determined.

By using the large number of fragments in the ordering library very short segments are generated, thus reducing the chance of the multiple appearance of the k−1 sequences which are the reasons for generation of the subfragments. Furthermore, longer segments, consisting of the various regions of the given fragment of the basic library, do not contain some of the repeated k−1 sequences. In every segment a connecting sequence (a connecting subfragment) is generated for a certain pair of the subfragments from the given fragment. The process of ordering consists of three steps: (1) generation of the k-tuple contents of each segment; (2) generation of subfragments in each segment; and (3) connection of the subfragments of the segments. Primary segments are defined as significant intersections and differences of k-tuple contents of a given fragment of the basic library with the k-tuple contents of the pools of the ordering library. Secondary (shorter) segments are defined as intersections and differences of the k-tuple contents of the primary segments.

There is a problem of accumulating both false positive and negative k-tuples in both the differences and intersections. The false negative k-tuples from starting sequences accumulate in the intersections (overlapping parts), as well as false positive k-tuples occurring randomly in both sequences, but not in the relevant overlapping region. On the other hand, the majority of false positives from either of the starting sequences is not taken up into intersections. This is an example of the reduction of experimental errors from individual fragments by using information from fragments overlapping with them. The false k-tuples accumulate in the differences for another reason. The set of false negatives from the original sequences are enlarged for false positives from intersections and the set of false positives for those k-tuples which are not included in the intersection by error, i.e. are false negative in the intersection. If the starting sequences contain 10% false negative data, the primary and secondary intersections will contain 19% and 28% false negative k-tuples, respectively. On the other hand, a mathematical expectation of 77 false positives may be predicted if the basic fragment and the pools have lengths of 500 bp and 10,000 bp, respectively. However, there is a possibility of recovering most of the "lost" k-tuples and of eliminating most of the false positive k-tuples.

First, one has to determine a basic content of the k-tuples for a given segment as the intersection of a given pair of the k-tuple contents. This is followed by including all k-tuples of the starting k-tuple contents in the intersection, which contain at one end k−1 and at the other end k−+ sequences which occur at the ends of two k-tuples of the basic set. This is done before generation of the differences thus preventing the accumulation of false positives in that process. Following that, the same type of enlargement of k-tuple set is applied to differences with the distinction that the borrowing is from the intersections. All borrowed k-tuples are eliminated from the intersection files as false positives.

The intersection, i.e. a set of common k-tuples, is defined for each pair (a basic fragment)×(a pool of ordering library). If the number of k-tuples in the set is significant it is enlarged with the false negatives according to the described rule. The primary difference set is obtained by subtracting from a given basic fragment the obtained intersection set. The false negative k-tuples are appended to the difference set by borrowing from the intersection set according to the described rule and, at the same time, removed from the intersection set as false positive k-tuples. When the basic fragment is longer than the pooled fragments, this difference can represent the two separate segments which somewhat reduces its utility in further steps. The primary segments are all generated intersections and differences of pairs (a basic fragment)×(a pool of ordering library) containing the significant number of k-tuples. K-tuple sets of secondary segments are obtained by comparison of k-tuple sets of all possible pairs of primary segments. The two differences are defined from each pair which produces the intersection with the significant number of k-tuples. The majority of available information from overlapped fragments is recovered in this step so that there is little to be gained from the third round of forming intersections and differences.

(2) Generation of the subfragments of the segments is performed identically as described for the fragments of the basic library.

(3) The method of connection of subfragments consists of sequentially determining the correctly linked pairs of subfragments among the subfragments from a given basic library fragment which have some overlapped ends. In the case of 4 relevant subfragments, two of which contain the same beginning and two having the same end, there are 4 different pairs of subfragments that can be connected. In general 2 are correct and 2 are wrong. To find correct ones, the presence of the connecting sequences of each pair is tested in the subfragments generated from all primary and secondary segments for a given basic fragment. The length and the position of the connecting sequence are chosen to avoid interference with sequences which occur by chance. They are k+2 or longer, and include at least one element 2 beside overlapping sequence in both subfragments of a given pair. The connection is permitted only if the two connecting sequences are found and the remaining two do not exist. The two linked subfragments replace former subfragments in the file and the process is cyclically repeated.

Repeated sequences are generated in this step. This means that some subfragments are included in linked subfragments more than once. They will be recognized by finding the relevant connecting sequence which engages one subfragment in connection with two different subfragments.

The recognition of misconnected subfragments generated in the processes of building pSFs and merging pSFs into longer subfragments is based on testing whether the sequences of subfragments from a given basic fragment exist in the sequences of subfragments generated in the segments for the fragment. The sequences from an incorrectly connected position will not be found indicating the misconnected subfragments.

Beside the described three steps in ordering of subfragments some additional control steps or steps applicable to specific sequences will be necessary for the generation of more complete sequence without mistakes.

The determination of which subfragment belongs to which segment is performed b comparison of contents of k-tuples in segments and subfragments. Because of the errors in the k-tuple contents (due to the primary error in pools and statistical errors due to the frequency of occurrences of k-tuples) the exact partitioning of subfragments is impossible. Thus, instead of "all or none" partition, the chance of coming from the given segment ($P(sf,s)$) is determined for each subfragment. This possibility is the function of the lengths of k-tuples, the lengths of subfragments, the lengths of fragments of ordering library, the size of the pool, and of the percentage of false k-tuples in the file:

$$P(sf,s) = (Ck-F)/Lsf,$$

where $Lsf$ is the length of subfragment, $Ck$ is the number of common k-tuples for a given subfragment/segment pair, and $F$ is the parameter that includes relations between lengths of k-tuples, fragments of basic library, the size of the pool, and the error percentage.

Subfragments attributed to a particular segment are treated as redundant short pSFs and are submitted to a process of unambiguous connection. The definition of unambiguous connection is slightly different in this case, since it is based on a probability that subfragments with overlapping end(s) belong to the segment considered. Besides, the accuracy of unambiguous connection is controlled by following the connection of these subfragments in other segments. After the connection in different segments, all of the obtained subfragments are merged together, shorter subfragments included within longer ones are eliminated, and the remaining ones are submitted to the ordinary connecting process. If the sequence is not regenerated completely, the process of partition and connection of subfragments is repeated with the same or less severe criterions of probability of belonging to the particular segment, followed by unambiguous connection.

Using severe criteria for defining unambiguous overlap, some information is not used. Instead of a complete sequence, several subfragments that define a number of possibilities for a given fragment are obtained. Using less severe criteria an accurate and complete sequence is generated. In a certain number of situations, e.g. an erroneous connection, it is possible to generate a complete, but an incorrect sequence, or to generate "monster" subfragments with no connection among them . Thus, for each fragment of the basic library one obtains: a) several possible solutions where one is correct and b) the most probable correct solution. Also, in a very small number of cases, due to the mistake in the subfragment generation process or due to the specific ratio of the probabilities of belonging, no unambiguous solution is generated or one, the most probable solution. These cases remain as incomplete sequences, or the unambiguous solution is obtained by comparing these data with other, overlapped fragments of basic library.

The described algorithm was tested on a randomly generated, 50 kb sequence, containing 40% GC to simulate the GC content of the human genome. In the middle part of this sequence were inserted various All, and some other repetitive sequences, of a total length of about 4 kb. To simulate an in vitro SBH experiment, the following operations were performed to prepare appropriate data.

Positions of sixty 5 kb overlapping "clones" were randomly defined, to simulate preparation of a basic library:

Positions of one thousand 500 bp "clones" were randomly determined to simulate making the ordering library. These fragments were extracted from the sequence. Random pools of 20 fragments were made, and k-tuple sets of pools were determined and stored on the hard disk. These data are used in the subfragment ordering phase: For the same density of clones 4 million clones in basic library and 3 million clones in ordering library are used for the entire human genome. The total number of 7 million clones is several fold smaller than the number of clones a few kb long for random cloning of almost all of genomic DNA and sequencing by a gel-based method.

From the data on the starts and ends of 5 kb fragments, 117 "informative fragments" were determined to be in the sequence. This was followed by determination of sets of overlapping k-tuples of which the single "informative fragment" consist. Only the subset of k-tuples matching a predetermined list were used. The list contained 65% 8-mers, 30% 9-mers, and 5% 10–12-mers. Processes of generation and the ordering of subfragments were performed on these data.

The testing of the algorithm was performed on the simulated data in two experiments. The sequence of 50 informative fragments was regenerated with the 100% correct data set (over 20,000 bp), and 26 informative fragments (about 10,000 bp) with 10% false k-tuples (5% positive and 5% negative ones).

In the first experiment, all subfragments were correct and in only one out of 50 informative fragments the sequence was not completely regenerated but remained in the form of 5 subfragments. The analysis of positions of overlapped fragments of ordering library has shown that they lack the information for the unique ordering of the 5 subfragments. The subfragments may be connected in two ways based on overlapping ends, 1-2-3-4-5 and 1-4-3-2-5. The only difference is the exchange of positions of subfragments 2 and 4. Since subfragments 2, 3, and 4 are relatively short (total of about 100 bp), the relatively greater chance existed, and occurred in this case, that none of the fragments of ordering library started or ended in the subfragment 3 region.

To simulate real sequencing, some false ("hybridization") data was included as input in a number of experiments. In oligomer hybridization experiments, under proposed conditions, the only situation producing unreliable data is the end mismatch versus full match hybridization. Therefore, in simulation only those k-tuples differing in a single element on either end from the real one were considered to be false positives. These "false" sets are made as follows. On the original set of a k-tuples of the informative fragment, a subset of 5% false positive k-tuples are added. False positive k-tuples are made by randomly picking a k-tuple from the set, copying it and altering a nucleotide on its beginning or end. This is followed by subtraction of a subset of 5% randomly chosen k-tuples. In this way the statistically expected number of the most complicated cases is generated in which the correct k-tuple is replaced with a k-tuple with the wrong base on the end.

Production of k-tuple sets as described leads to up to 10% of false data. This value varies from case to case, due to the randomness of choice of k-tuples to be copied, altered, and erased. Nevertheless, this percentage 3–4 times exceeds the amount of unreliable data in real hybridization experiments. The introduced error of 10% leads to the two fold increase in the number of subfragments both in fragments of basic library (basic library informative fragments) and in segments. About 10% of the final subfragments have a wrong base at the end as expected for the k-tuple set which contains false positives (see generation of primary subfragments). Neither the cases of misconnection of subfragments nor subfragments with the wrong sequence were observed. In 4 informative fragments out of 26 examined in the ordering process the complete sequence was not regenerated. In all 4 cases the sequence was obtained in the form of several longer subfragments and several shorter subfragments contained in the same segment. This result shows that the algorithmic principles allow working with a large percentage of false data.

The success of the generation of the sequence from its k-tuple content may be described in terms of completeness and accuracy. In the process of generation, two particular situations can be defined: 1) Some part of the information is missing in the generated sequence, but one knows where the ambiguities are and to which type they belong, and 2) the regenerated sequence that is obtained does not match the sequence from which the k-tuple content is generated, but the mistake can not be detected. Assuming the algorithm is developed to its theoretical limits, as in the use of the exact k-tuple sets, only the first situation can take place. There the incompleteness results in a certain number of subfragments that may not be ordered unambiguously and the problem of determination of the exact length of monotonous sequences, i.e. the number of perfect tandem repeats.

With false k-tuples, incorrect sequence may be generated. The reason for mistakes does not lie in the shortcomings of the algorithm, but in the fact that a given content of k-tuples unambiguously represents the sequence that differs from the original one. One may define three classes of error, depending on the kind of the false k-tuples present in the file. False negative k-tuples (which are not accompanied with the false positives) produce "deletions". False positive k-tuples are producing "elongations (unequal crossing over)". False positives accompanied with false negatives are the reason for generation of "insertions", alone or combined with "deletions". The deletions are produced when all of the k-tuples (or their majority) between two possible starts of the subfragments are false negatives. Since every position in the sequence is defined by k k-tuples, the occurrence of the deletions in a common case requires k consecutive false negatives. (With 10% of the false negatives and k=8, this situation takes place after every 108 elements). This situation is extremely infrequent even in mammalian genome sequencing using random libraries containing ten genome equivalents.

Elongation of the end of the sequence caused by false positive k-tuples is the special case of "insertions", since the end of the sequence can be considered as the endless linear array of false negative k-tuples. One may consider a group of false positive k-tuples producing subfragments longer than one k-tuple. Situations of this kind may be detected if subfragments are generated in overlapped fragments, like random physical fragments of the ordering library. An insertion, or insertion in place of a deletion, can arise as a result of specific combinations of false positive and false negative k-tuples. In the first case, the number of consecutive false negatives is smaller than k. Both cases require several overlapping false positive k-tuples. The insertions and deletions are mostly theoretical possibilities without sizable practical repercussions since the requirements in the number and specificity of false k-tuples are simply too high.

In every other situation of no meeting the theoretical requirement of the minimal number an the kind of the false positive and/or negatives, mistakes in the k-tuples content may produce only the lesser completeness of a generated sequence.

What is claimed is:

1. A method of analyzing nucleic acids by hybridization, comprising the steps of:

contacting a first plurality of different nucleic acid segments disposed on a first sector of a substrate with a first hybridization oligonucleotide, wherein said first plurality of nucleic acids is arranged on said first sector in a spatially identifiable array, under conditions that discriminate between a perfect match and a single base mismatch in the hybridization of a member of said first array of nucleic acid segments to the informational portion of said first hybridization oligonucleotide;

contacting a second plurality of different nucleic acid segments disposed on a second sector of the substrate with a second hybridization oligonucleotide, wherein said second plurality of nucleic acids is arranged on said second sector in a spatially identifiable array, under conditions that discriminate between a perfect match and a single base mismatch in this hybridization of a member of said second array of nucleic acid segments to the informational portion of said second hybridization oligonucleotide, wherein said second hybridization oligonucleotide differs in sequence from said first hybridization oligonucleotide;

wherein said first plurality of nucleic acid segments is not contacted with said second hybridization oligonucleotide;

detecting hybridization of a hybridization oligonucleotide to a nucleic acid segment; and analyzing the result.

2. The method as recited in claim 1 wherein said first contacting step comprises the step of applying a plurality of contiguously hybridizing oligonucleotides.

3. The method as recited in claim 1 wherein said second contacting step comprises the step of applying a plurality of contiguously hybridizing oligonucleotides.

4. The method as recited in claim 2 further comprising the step of ligating at least two of said plurality of contiguously hybridizing oligonucleotides.

5. The method as recited in claim 3 further comprising the step of ligating at least two of said plurality of contiguously hybridizing oligonucleotides.

6. The method as recited in claim 1 wherein said first contacting step comprises the step of applying a plurality of competitively hybridizing oligonucleotides having overlapping nucleic acid sequences.

7. The method as recited in claim 1 wherein said second contacting step comprises the step of applying a plurality of competitively hybridizing oligonucleotides having overlapping nucleic acid sequences.

8. The method as recited in claim 1 wherein a least two of said first plurality of nucleic acid segments are disposed as a mixture.

9. The method as recited in claim 1 wherein a least two of said second plurality of nucleic acid segments are disposed as a mixture.

10. The method as recited in claim 1 further comprising the step of selecting deoxyribonucleotide oligonucleotides.

11. The method as recited in claim 1 further comprising the step of selecting ribonucleotide oligonucleotides.

12. The method as recited in claim 1 further comprising the step of multiplex labeling of oligonucleotides.

13. The method as recited in claim 1 further comprising the step of degrading a label on an unhybridized oligonucleotide.

14. The method as recited in claim 1 further comprising the step of stripping the substrate of oligonucleotides for reuse of said pluralities of nucleic acid segments.

15. A method for analyzing a plurality of nucleic acids from a plurality of subjects, comprising the steps of:

providing a substrate comprising the nucleic acids, wherein the nucleic acids are disposed on a plurality of sectors on the substrate, and wherein different nucleic acids are arranged on each sector in a spatially identifiable array;

contacting the nucleic acids with a plurality of oligonucleotide probes under conditions that discriminate between a perfect match and a single base mismatch in the hybridization of a member of said plurality of nucleic acid segments to the informational portion of a member of said plurality of oligonucleotides, wherein the different nucleic acids on a first sector are contacted with a first probe and the nucleic acids on a different second sector are contacted with a second probe, wherein the second probe differs in sequence from the first probe and the first sector is not contacted with the second probe; and determining which probes bind to the nucleic acids, thereby identifying single nucleotide polymorphisms among the plurality of samples.

16. The method of claim 15, wherein the subjects all share a particular phenotype.

17. The method of claim 16, wherein the nucleic acids represent a large number of genes from the subject.

18. The method of claim 17, further comprising the step of determining which mutations are shared by several subjects.

19. The method of claim 15, wherein the subjects are members of a species.

20. The method of claim 19, wherein the subjects have been exposed to a plurality of different environmental conditions.

21. The method of claim 15, wherein the subjects are members of a plurality of species.

22. The method of claim 21, wherein the nucleic acids include an evolutionarily conserved DNA sequence.

23. A method for analyzing a nucleic acid, comprising the steps of:

providing a substrate comprising the nucleic acid, wherein the nucleic acid is disposed on a plurality of sectors on the substrate, and wherein each sector comprises a spatially identifiable array of immobilized nucleic acids;

contacting the nucleic acid with a plurality of oligonucleotides under conditions that discriminate between a perfect match and a single base mismatch in the hybridization of the nucleic acid to the informational portion of a member of said plurality of oligonucleotides, wherein the nucleic acid in a first sector of the substrate is contacted with a first oligonucleotide and the nucleic acid in a second sector of the substrate is contacted with a second oligonucleotide, wherein the second oligonucleotide differs in sequence from the first oligonucleotide and the first sector is not contacted with the second oligonucleotide; and determining which oligonucleotides bind to the nucleic acid.

24. The method of claim 23, wherein the plurality of oligonucleotides contains a first set of oligonucleotides having the formula $N_{Xa}B_{Ya}N_{Za}$ wherein the $B_{Ya}$ portions are capable of forming perfectly matched duplexes with a fragment of the nucleic acid and a second set of oligonucleotides having the formula $N_{Xb}B_{Yb}N_{Zb}$ wherein the $B_{Yb}$ portions are capable of forming mismatched duplexes with a fragment of the nucleic acid, wherein the fragment has a known sequence.

25. The method of claim 24, wherein the fragment is part of an STS.

26. The method of claim 24, wherein the fragment is part of an antibiotic resistance gene.

27. The method of claim 24, wherein the fragment is part of an HIV.

28. The method of claim 23, wherein the plurality of oligonucleotide contains a plurality of paired sets of first oligonucleotides having the formula $N_{Xa}B_{Ya}N_{Za}$ wherein the $B_{Ya}$ portions are capable of forming perfectly matched duplexes with a plurality of fragments in the nucleic acid and second oligonucleotides having the formula $N_{Xb}B_{Yb}N_{Zb}$ wherein the $B_{Yb}$ portions are capable of forming mismatched duplexes with a plurality of fragments in the nucleic acid, wherein the fragments have known sequences.

29. The method of claim 28, wherein the plurality of fragments are from an HIV.

30. The method of claim 24, wherein the fragment contains a single nucleotide polymorphism.

31. The method of claim 28, wherein the fragments contain a plurality of single nucleotide polymorphisms.

32. The method of claim 31, wherein each fragment has a different single nucleotide polymorphism.

33. The method of claim 28, wherein the fragment is part of an STS.

34. The method of claim 28, wherein the fragment is part of an antibiotic resistance gene.

35. The method of claim 24 wherein the amount of nucleic acid is determined by comparing the intensity of hybridization for several of the positive oligonucleotides with a sample containing the nucleic acid and with a control sample containing a known amount of DNA.

36. The method of claim 28, wherein the amount of nucleic acid is determined by comparing the intensity of hybridization for several of the first oligonucleotide with a sample containing the nucleic acid and with a control sample containing a known amount of DNA.

37. The method according to either claim 1 or claim 23, wherein the nucleic acids arrayed on said sector are derived from a subject.

* * * * *

UNITED STATES PATENT AND TRADEMARK OFFICE
CERTIFICATE OF CORRECTION

PATENT NO.   : 6,270,961 B1
DATED        : August 7, 2001
INVENTOR(S)  : Radoje Drmanac It is certified that error appears in the above-identified patent and that said Letters Patent is hereby corrected as shown below:

<u>Column 36,</u>
Line 42, replace "Thc" with -- The --.
Lines 62 and 65, replace "a least" with -- at least --.

<u>Column 38,</u>
Line 55, replace "oligonucleotide" with -- oligonucleotides --.

Signed and Sealed this

Fourteenth Day of January, 2003

JAMES E. ROGAN
*Director of the United States Patent and Trademark Office*